(12) United States Patent
Sawada et al.

(10) Patent No.: US 10,525,418 B2
(45) Date of Patent: Jan. 7, 2020

(54) PURIFICATION METHOD FOR PURIFYING LIQUID, PURIFICATION METHOD FOR PURIFYING SILICON COMPOUND-CONTAINING LIQUID, METHOD FOR PRODUCING SILYLATING AGENT LIQUID, FILM FORMING MATERIAL OR DIFFUSING AGENT COMPOSITION, FILTER MEDIUM AND FILTER DEVICE

(71) Applicant: Tokyo Ohka Kogyo Co., Ltd., Kanagawa (JP)

(72) Inventors: Yoshihiro Sawada, Kanagawa (JP); Tsukasa Sugawara, Kanagawa (JP)

(73) Assignee: TOKYO OHKA KOGYO CO., LTD., Kanagawa (JP)

( * ) Notice: Subject to any disclaimer, the term of this patent is extended or adjusted under 35 U.S.C. 154(b) by 0 days.

(21) Appl. No.: 15/772,931

(22) PCT Filed: Oct. 28, 2016

(86) PCT No.: PCT/JP2016/082140
§ 371 (c)(1),
(2) Date: May 2, 2018

(87) PCT Pub. No.: WO2017/082088
PCT Pub. Date: May 18, 2017

(65) Prior Publication Data
US 2018/0311622 A1 Nov. 1, 2018

(30) Foreign Application Priority Data

Nov. 10, 2015 (JP) ................. 2015-220512

(51) Int. Cl.
| | |
|---|---|
| *B01D 69/02* | (2006.01) |
| *C08J 9/26* | (2006.01) |
| *H01L 21/225* | (2006.01) |
| *B01D 67/00* | (2006.01) |
| *C07F 7/20* | (2006.01) |
| *C07F 7/10* | (2006.01) |
| *C07F 7/18* | (2006.01) |
| *C09D 179/08* | (2006.01) |
| *C08G 73/10* | (2006.01) |
| *H01L 21/22* | (2006.01) |
| *B01D 71/64* | (2006.01) |
| *B01D 61/14* | (2006.01) |
| *C08G 73/14* | (2006.01) |

(52) U.S. Cl.
CPC ........... *B01D 69/02* (2013.01); *B01D 67/003* (2013.01); *B01D 67/0093* (2013.01); *C07F 7/10* (2013.01); *C07F 7/18* (2013.01); *C07F 7/20* (2013.01); *C08G 73/105* (2013.01); *C08G 73/1071* (2013.01); *C08J 9/26* (2013.01); *C09D 179/08* (2013.01); *H01L 21/225* (2013.01); *H01L 21/2225* (2013.01); *B01D 61/14* (2013.01); *B01D 71/64* (2013.01); *B01D 2325/021* (2013.01); *C08G 73/14* (2013.01); *C08J 2379/08* (2013.01)

(58) Field of Classification Search
None
See application file for complete search history.

(56) References Cited

U.S. PATENT DOCUMENTS

| | | | |
|---|---|---|---|
| 2005/0136692 | A1 | 6/2005 | Fujii et al. |
| 2006/0014098 | A1 | 1/2006 | Hada et al. |
| 2009/0311874 | A1 | 12/2009 | Tomita et al. |
| 2010/0075504 | A1 | 3/2010 | Tomita et al. |

(Continued)

FOREIGN PATENT DOCUMENTS

| | | |
|---|---|---|
| JP | 2005-171067 | 6/2005 |
| JP | 2008-56737 | 3/2008 |

(Continued)

OTHER PUBLICATIONS

International Search Report dated Jan. 24, 2017 in International (PCT) Application No. PCT/JP2016/082140.

*Primary Examiner* — Clinton A Brooks
*Assistant Examiner* — Kofi Adzamli
(74) *Attorney, Agent, or Firm* — Wenderoth, Lind & Ponack, L.L.P.

(57) ABSTRACT

To provide: a purification method which uses a polyimide and/or polyamide imide porous membrane that exhibits excellent removal performance for impurities such as metals, and wherein a liquid that is a silylating agent liquid, a film forming material or a diffusing agent composition is an object to be purified; a purification method for purifying a silicon compound-containing liquid that contains a silicon compound which is capable of producing a silanol group by hydrolysis; a method for producing a silylating agent liquid, a film forming material or a diffusing agent composition, which uses the purification method; a filter medium which is composed of the above-described porous membrane; and a filter device which comprises the above-described porous membrane. A purification method for purifying a liquid, which comprises a step in which some or all of the liquid is caused to permeate through a polyimide and/or polyamide imide porous membrane having communicating pores from one side to the other side by means of differential pressure, and wherein the liquid is a silylating agent liquid, a film forming material or a diffusing agent composition that is used for diffusing a dopant into a semiconductor substrate.

18 Claims, No Drawings

(56) References Cited

U.S. PATENT DOCUMENTS

| | | | |
|---|---|---|---|
| 2010/0240219 A1 | 9/2010 | Tomita et al. | |
| 2010/0297551 A1* | 11/2010 | Teranishi | C08F 220/18 |
| | | | 430/270.1 |
| 2012/0017934 A1 | 1/2012 | Kumon et al. | |
| 2015/0246322 A1* | 9/2015 | Larue | B01D 69/02 |
| | | | 210/650 |
| 2016/0185932 A1 | 6/2016 | Sugawara | |

FOREIGN PATENT DOCUMENTS

| | | |
|---|---|---|
| JP | 2009-138083 | 6/2009 |
| JP | 2010-114414 | 5/2010 |
| JP | 2010-270185 | 12/2010 |
| JP | 4637476 | 2/2011 |
| JP | 2015-165009 | 9/2015 |
| WO | 2011/155407 | 12/2011 |
| WO | 2015/020101 | 2/2015 |

* cited by examiner

PURIFICATION METHOD FOR PURIFYING LIQUID, PURIFICATION METHOD FOR PURIFYING SILICON COMPOUND-CONTAINING LIQUID, METHOD FOR PRODUCING SILYLATING AGENT LIQUID, FILM FORMING MATERIAL OR DIFFUSING AGENT COMPOSITION, FILTER MEDIUM AND FILTER DEVICE

TECHNICAL FIELD

The present invention relates to a purification method for purifying a liquid that is a silylating agent liquid, a film forming material or a diffusing agent composition, as an object to be purified, using a polyimide and/or polyamideimide porous membrane; a purification method for purifying a silicon compound-containing liquid that includes a silicon compound capable of producing a silanol group by hydrolysis, as an object to be purified; a method for producing a silylating agent liquid, a film forming material or a diffusing agent composition using the purification method; a filter medium which is composed of the polyimide and/or polyamideimide porous membrane; as well as a filter device including the polyimide and/or polyamideimide porous membrane.

BACKGROUND ART

In semiconductor devices, with the increasing demand for higher performance, higher functionality, and lower power consumption, circuit patterns have been increasingly miniaturized. Accordingly, demand for removal of contaminant metals that would reduce the production yield has been significantly increased. Therefore, it is desirable that contaminant metals such as iron or zinc be not contained in a silylating agent liquid for forming a protective film for imparting hydrophobicity to a substrate (see, for example, Patent Document 1), a material for forming a fine membrane (see, for example, Patent Document 2), and a diffusing agent composition that is used for diffusing a dopant into a semiconductor substrate.

Such chemical solutions for use in the process of manufacturing semiconductor devices are cleaned beforehand to remove contaminant metals such as iron and zinc by way of a filter device or the like. The filter device usually includes a filter medium with a porous membrane.

Since impurities such as metal ions are removed, porous membranes capable of removing minute substances such as nanoparticles are desirable. Nylon, polyethylene, polypropylene, PTFE, and the like, are typically used as filter membranes capable of removing impurities from a chemical solution or a resin material to be used for a semiconductor device or the like. For example, it is known that organic impurities can also be removed by way of a filter membrane of nylon or the like (for example, see Patent Document 3).

Patent Document 1: Japanese Unexamined Patent Application, Publication No. 2010-114414
Patent Document 2: Japanese Unexamined Patent Application, Publication No. 2005-171067
Patent Document 3: Japanese Patent No. 4637476

DISCLOSURE OF THE INVENTION

Problems to be Solved by the Invention

However, membranes made of nylon have problems such as having poor acid resistance, thus being difficult to be cleaned with an acid, and being difficult to remove impurities mixed in or adhered to the filter itself. Further, membranes made of polyethylene have a problem of a low removal rate of impurities such as iron and zinc that should be removed from the chemical solution used in the manufacturing process of semiconductor devices.

The porous membranes used in filter media are industrially required to be capable of treating at a certain flow rate. When the flow rate is increased, however, the removal performance for impurities such as metals tends to be lowered. Thus, it has been difficult to achieve both the flow rate and the capability of removal performance for impurities.

The present invention has been made in view of the above circumstances, and it is an object of the present invention to provide a purification method for purifying a liquid that is a silylating agent liquid, a film forming material or a diffusing agent composition, as an object to be purified, using a polyimide and/or polyamideimide porous membrane that exhibits excellent removal performance for impurities such as metals; a purification method for purifying a silicon compound-containing liquid, which includes a silicon compound capable of producing a silanol group by hydrolysis, as an object to be purified; a method for producing a silylating agent liquid, a film forming material or a diffusing agent composition using the purification methods; a filter medium which is composed of the porous membrane; as well as a filter device including the porous membrane.

Means for Solving the Problems

The present inventors have found that a polyimide and/or polyamideimide porous membrane having communicating pores exhibits excellent removal performance for impurities such as metals by virtue of its porous structure, and they have completed the present invention.

A first aspect of the present invention is a purification method for purifying a liquid as an object to be purified, the method including allowing some or all of the liquid to permeate through a polyimide and/or polyamideimide porous membrane having communicating pores from one side to the other side by way of a differential pressure, wherein the liquid is a silylating agent liquid, a film forming material, or a diffusing agent composition that is used for diffusing a dopant into a semiconductor substrate.

A second aspect of the present invention is a purification method for purifying a silicon compound-containing liquid as an object to be purified, the method including allowing some or all of the silicon compound-containing liquid to permeate through a polyimide and/or polyamideimide porous membrane having communicating pores from one side to the other side by way of a differential pressure, wherein the silicon compound-containing liquid includes a silicon compound capable of producing a silanol group by hydrolysis.

A third aspect of the present invention is a method for producing a silylating agent liquid, a film forming material or a diffusing agent composition using the purification method for purifying a liquid as an object to be purified according to the first aspect of the present invention or the purification method for purifying a silicon compound-containing liquid as an object to be purified according to the second aspect of the present invention.

A fourth aspect of the present invention is a filter medium which is composed of the polyimide and/or polyamideimide porous membrane to be used for the purification method for purifying a liquid as an object to be purified according to the first aspect of the present invention or the purification method for purifying a silicon compound-containing liquid as an object to be purified according to the second aspect of the present invention.

A fifth aspect of the present invention is a filter device including the polyimide and/or polyamideimide porous membrane to be used for the purification method for purifying a liquid as an object to be purified according to the first aspect of the present invention or the purification method for purifying a silicon compound-containing liquid as an object to be purified according to the second aspect of the present invention.

Effects of the Invention

The present invention can provide a purification method for purifying a liquid using a polyimide and/or polyamideimide porous membrane excellent in capability of removing metal, a method for producing a chemical solution or a cleaning solution using the purification method, a filter medium which is composed of the porous membrane, and a filter device including the porous membrane.

PREFERRED MODE FOR CARRYING OUT THE INVENTION

Embodiments of the present invention will be hereinafter described in further detail. However, the present invention is not necessarily limited to the following embodiments, and can be implemented as appropriately modified within the scope of the object of the present invention.

[Purification Method for Purifying Liquid that is Silylating Agent Liquid, Film Forming Material, or Diffusing Agent Composition that is Used for Diffusing Dopant into Semiconductor Substrate as Object to be Purified]

The purification method for purifying a liquid as an object to be purified according to the first aspect includes allowing some or all of the liquid to permeate through a polyimide and/or polyamideimide porous membrane having communicating pores from one side to the other side by way of a differential pressure. The liquid is a silylating agent liquid, a film forming material, or a diffusing agent composition that is used for diffusing a dopant into a semiconductor substrate. The purification method for purifying a liquid as an object to be purified according to the first aspect preferably uses the filter medium which is composed of the polyimide and/or polyamideimide porous membrane, or the filter device including the polyimide and/or polyamideimide porous membrane.

[Purification Method for Purifying Silicon Compound-Containing Liquid as Object to be Purified, which Includes Silicon Compound Capable of Producing Silanol Group by Hydrolysis]

The purification method for purifying a silicon compound-containing liquid as an object to be purified according to the second aspect, includes allowing some or all of the silicon compound-containing liquid to permeate through a polyimide and/or polyamideimide porous membrane having communicating pores from one side to the other side by way of a differential pressure. The silicon compound-containing liquid includes a silicon compound capable of producing a silanol group by hydrolysis. The purification method for purifying a silicon compound-containing liquid as an object to be purified according to the second aspect preferably uses the filter medium which is composed of the polyimide and/or polyamideimide porous membrane, or the filter device including the polyimide and/or polyamideimide porous membrane. In the purification method for purifying a silicon compound-containing liquid as an object to be purified according to the second aspect, it is preferable that the silicon compound-containing liquid is a silylating agent liquid, a film forming material, or a diffusing agent composition that is used for diffusing a dopant into a semiconductor substrate.

<Silylating Agent Liquid>

Types of the above-mentioned silylating agent liquids as an object to be purified are not particularly limited as long as it can make a substrate surface hydrophobic, and can be appropriately selected from silylating agent liquids conventionally used for making various materials water-repellent or hydrophobic. In this specification, "making hydrophobic" is a concept including making water-repellent. The silylating agent liquid as an object to be purified preferably includes a silicon compound capable of producing a silanol group by hydrolysis. The silicon compound is more preferably a silylating agent represented by the following general formula (1).

(In the formula (1), $R^{a1}$ each independently represents a monovalent organic group including a monovalent hydrocarbon group having 1 to 18 carbon atoms in which some or all of hydrogen atoms may be substituted with a fluorine atom, $X^1$ each independently represents a monovalent functional group in which an atom bonded to a silicon atom is nitrogen, a is an integer of 1 to 3, b is an integer of 0 to 2, and a total of a and b is 1 to 3.)

[Silylating Agent]

Suitable examples of the silylating agent include silylating agents represented by the following general formulae (1-1) to (1-8), and cyclic silazane compounds. Hereinafter, the silylating agents represented by the following general formulae (1-1) to (1-8) and the cyclic silazane compounds will be described sequentially.

Silylating agent represented by general formula (1-1)

[Chem. 11]

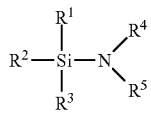

(1-1)

In the general formula (1-1), $R^1$, $R^2$ and $R^3$ each independently represent a hydrogen atom, a halogen atom, or an organic group. The total number of carbon atoms of $R^1$, $R^2$ and $R^3$ is 1 or more. $R^4$ represents a hydrogen atom, or a saturated or unsaturated chain hydrocarbon group. $R^5$ represents a hydrogen atom, a saturated or unsaturated chain hydrocarbon group, a saturated or unsaturated non-aromatic cyclic hydrocarbon group, or non-aromatic heterocyclic group. $R^4$ and $R^5$ may be bonded to each other to form non-aromatic heterocycle including a nitrogen atom.

When $R^1$, $R^2$ and $R^3$ are a halogen atom, the halogen atom is preferably a chlorine atom, a bromine atom, an iodine atom, and a fluorine atom.

When $R^1$, $R^2$ and $R^3$ are an organic group, the organic group may include hetero atom other than a carbon atom. Types of the hetero atom that may be included in the organic group are not particularly limited within a range where the objects of the present invention are not impaired. Preferable examples of the hetero atom that may be included in the organic group include N, O, and S. When $R^1$, $R^2$ and $R^3$ are an organic group, the total of the number of carbon atoms and the number of hetero atoms included in the organic group is not particularly limited as long as the total number of carbon atoms of $R^1$, $R^2$ and $R^3$ is 1 or more. The total of the number of carbon atoms and the number of hetero atoms included in the organic group, when $R^1$, $R^2$ and $R^3$ are an organic group, is preferably 1 to 10, more preferably 1 to 8, and particularly preferably 1 to 3. When $R^1$, $R^2$ and $R^3$ are an organic group, preferable examples of the organic group include a saturated or unsaturated chain hydrocarbon group, an aralkyl group, and an aromatic hydrocarbon group. Suitable examples of the saturated or unsaturated chain hydrocarbon group may include a methyl group, an ethyl group, a vinyl group, an n-propyl group, an isopropyl group, an allyl group, a 1-propenyl group, an isopropenyl group, an n-butyl group, a sec-butyl group, a tert-butyl group, a 3-butenyl group, an n-pentyl group, an isopentyl group, a sec-pentyl group, a tert-pentyl group, an n-hexyl group, an n-heptyl group, an n-octyl group, an n-nonyl group, an n-decyl group, and the like. Among these chain hydrocarbon groups, a methyl group, an ethyl group, a vinyl group, an n-propyl group, and an allyl group are preferable, a methyl group, an ethyl group, and a vinyl group are particularly preferable. Suitable examples of the aralkyl group include a benzyl group, a phenyl ethyl group, a phenyl propyl group, an α-naphthyl methyl group, and a β-naphthyl methyl group. Suitable examples of the aromatic hydrocarbon group include a phenyl group, an α-naphthyl group, and a β-naphthyl group.

When $R^4$ is a saturated or unsaturated chain hydrocarbon group, the number carbon of atoms of the saturated or unsaturated chain hydrocarbon group is not particularly limited within a range where the objects of the present invention are not impaired. When $R^4$ is a saturated or unsaturated chain hydrocarbon group, the number of carbon atoms of the saturated or unsaturated chain hydrocarbon group is preferably 1 to 10, more preferably 1 to 8, and particularly preferably 1 to 3. Suitable examples when $R^4$ is a saturated or unsaturated chain hydrocarbon group are the same as the saturated or unsaturated chain hydrocarbon groups listed as suitable examples of $R^1$, $R^2$ and $R^3$.

When $R^5$ is a saturated or unsaturated chain hydrocarbon group, a saturated or unsaturated chain hydrocarbon group is the same as that in $R^4$. When $R^5$ is a saturated or unsaturated cyclic hydrocarbon group, the number of carbon atoms of the saturated or unsaturated cyclic hydrocarbon groups is not particularly limited within a range where the objects of the present invention are not impaired. When $R^5$ is a saturated or unsaturated non-aromatic cyclic hydrocarbon group, the number of carbon atoms of the saturated or unsaturated cyclic hydrocarbon groups is preferably 3 to 10, more preferably 3 to 6, and particularly preferably 5 or 6. Suitable examples when $R^5$ is a saturated or cyclic hydrocarbon group include a cyclopropyl group, a cyclobutyl group, a cyclopentyl group, a cyclohexyl group, a cyclopentyl group, and a cyclooctyl group. When $R^5$ is a non-aromatic heterocyclic group, the hetero atom included in the non-aromatic heterocyclic group is not particularly limited within a range where the objects of the present invention are not impaired. When $R^5$ is a non-aromatic heterocyclic group, suitable hetero atoms included in the non-aromatic heterocyclic group include N, O, and S. When $R^5$ is a non-aromatic heterocyclic group, the total number of carbon atoms and the hetero atoms included in the non-aromatic heterocyclic group are not particularly limited within a range where the objects of the present invention are not impaired. When $R^5$ is a non-aromatic heterocyclic group, the total number of carbon atoms and the hetero atoms included in the non-aromatic heterocyclic group is preferably 3 to 10, more preferably 3 to 6, and particularly preferably 5 or 6. Suitable examples when $R^5$ is a non-aromatic heterocyclic group include a pyrrolidine-1-yl group, a piperidine-1-yl group, a piperazine-1-yl group, a morpholine-1-yl group, and a thiomorpholine-1-yl group.

The number of atoms included in the non-aromatic heterocyclic group formed when $R^4$ and $R^5$ are bonded to each other is not particularly limited within a range where the objects of the present invention are not impaired. The non-aromatic heterocyclic group formed when $R^4$ and $R^5$ are bonded to each other is preferably 3-membered ring to 10-membered ring, and more preferably 5-membered ring or 6-membered ring. The types of hetero atoms other than the carbon atoms included in the non-aromatic heterocyclic group when $R^4$ and $R^5$ are bonded to each other are not particularly limited within a range where the objects of the present invention are not impaired. Suitable examples of the hetero atoms included in the non-aromatic heterocyclic group when $R^4$ and $R^5$ are bonded to each other include N, O, and S. Suitable examples of the non-aromatic heterocycle when $R^4$ and $R^5$ are bonded to each other include pyrrolidine, piperidine, piperazine, morpholine, and thiomorpholine.

Specific examples of the silylating agent represented by the general formula (1-1) include N,N-dimethylamino trimethylsilane, N,N-dimethyl amino dimethyl silane, N,N-dimethylamino monomethylsilane, N,N-diethylamino trimethylsilane, t-butylamino trimethylsilane, allylamino trimethylsilane, trimethylsilyl acetamido, N,N-dimethylamino dimethyl vinyl silane, N,N-dimethylamino dimethyl propyl silane, N,N-dimethylamino dimethyloctylsilane, N,N-dimethylamino dimethyl phenylethylsilane, N,N-dimethylamino dimethylphenylsilane, N,N-dimethylamino dimethyl-t-butyl silane, N,N-dimethylamino triethylsilane, trimethylsilanamine, and the like.

Silylating agent represented by general formula (1-2)

[Chem. 2]

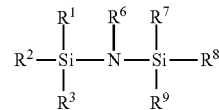

(1-2)

In the general formula (1-2), $R^1$, $R^2$ and $R^3$ are the same as in the general formula (1-1). $R^6$ represents a hydrogen atom, a methyl group, a trimethylsilyl group, or a dimethylsilyl group. $R^7$, $R^8$ and $R^9$ each independently represent a hydrogen atom or an organic group. The total number of carbon atoms of $R^7$, $R^8$ and $R^9$ is 1 or more.

When $R^7$, $R^8$ and $R^9$ are an organic group, the organic group is the same as an organic group when $R^1$, $R^2$ and $R^3$ are an organic group.

Specific examples of the silylating agent represented by the general formula (1-2) include hexamethyldisilazane, N-methylhexamethyldisilazane, 1,1,3,3-tetramethyl disilazane, 1,3-dimethyl disilazane, 1,3-di-n-octyl-1,1,3,3-tetramethyl disilazane, 1,3-divinyl-1,1,3,3,-tetramethyl disilazane, tris(dimethyl silyl) amine, tris(trimethylsilyl)amine, 1-ethyl-1,1,3,3,3-pentamethyl disilazane, 1-vinyl-1,1,3,3,3-pentamethyl disilazane, 1-propyl-1,1,3,3,3-pentamethyl disilazane, 1-phenyl ethyl-1,1,3,3,3-pentamethyl disilazane, 1-tert-butyl-1,1,3,3,3-pentamethyl disilazane, 1-phenyl-1,1,3,3,3-pentamethyl disilazane, 1,1,1-trimethyl-3,3,3-triethyl disilazane, and the like.

Silylating agent represented by general formula (1-3)

[Chem. 3]

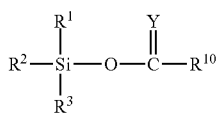

(1-3)

In the general formula (1-3), $R^1$, $R^2$ and $R^3$ are the same as those in the above general formula (1-1). Y represents O, $CHR^{11}$, $CHOR^{11}$, $CR^{11}R^{11}$, or $NR^{12}$. $R^{10}$ and $R^{11}$ each independently represent a hydrogen atom, a saturated or unsaturated chain hydrocarbon group, a saturated or unsaturated non-aromatic cyclic hydrocarbon group, a trialkylsilyl group, a trialkylsiloxy group, an alkoxy group, a phenyl group, a phenyl ethyl group, or an acetyl group. $R^{12}$ represents a hydrogen atom, an alkyl group, or a trialkylsilyl group.

When $R^{10}$ and $R^{11}$ are a saturated or unsaturated chain hydrocarbon group or a saturated or unsaturated non-aromatic cyclic hydrocarbon group, a saturated or unsaturated chain hydrocarbon group and a saturated or unsaturated non-aromatic cyclic hydrocarbon group are the same as a case where $R^5$ in the general formula (1-1) is a saturated or unsaturated chain hydrocarbon group or a saturated or unsaturated non-aromatic cyclic hydrocarbon group.

When $R^{10}$ and $R^{11}$ are a trialkylsilyl group, a trialkylsiloxy group, or an alkoxy group, the number of carbon atoms included in these groups is not particularly limited within a range where the objects of the present invention are not impaired. The number of carbon atoms of the alkyl group included in these groups is preferably 1 to 10, more preferably 1 to 8, and particularly preferably 1 to 3. Suitable examples of the alkyl group included in these groups include a methyl group, an ethyl group, an n-propyl group, an isopropyl group, an n-butyl group, a sec-butyl group, a tert-butyl group, an n-pentyl group, an isopentyl group, a sec-pentyl group, a tert-pentyl group, an n-hexyl group, an n-heptyl group, an n-octyl group, an n-nonyl group, an n-decyl group, and the like. Among these alkyl groups, a methyl group, an ethyl group, and an n-propyl group are more preferable, and a methyl group and an ethyl group are particularly preferable.

When $R^{12}$ is an alkyl group or a trialkylsilyl group, the number of carbon atoms of an alkyl group included in the alkyl group or the trialkylsilyl group is not particularly limited within a range where the objects of the present invention are not impaired. The number of carbon atoms of an alkyl group included in the alkyl group or the trialkylsilyl group is preferably 1 to 10, more preferably 1 to 8, and particularly preferably 1 to 3. Suitable examples of the alkyl group included in the alkyl group or the trialkylsilyl group include a methyl group, an ethyl group, an n-propyl group, an isopropyl group, an n-butyl group, a sec-butyl group, a tert-butyl group, an n-pentyl group, an isopentyl group, a sec-pentyl group, a tert-pentyl group, an n-hexyl group, an n-heptyl group, an n-octyl group, an n-nonyl group, and an n-decyl group, and the like. Among these alkyl groups, a methyl group, an ethyl group, and an n-propyl group are more preferable, and a methyl group and an ethyl group are particularly preferable.

Specific examples of the silylating agent represented by the general formula (1-3) include trimethylsilyl acetate, dimethylsilyl acetate, monomethylsilyl acetate, trimethylsilyl propionate, trimethylsilyl butyrate, trimethylsilyl-2-butenoate, and the like.

Silylating agent represented by general formula (1-4)

[Chem. 4]

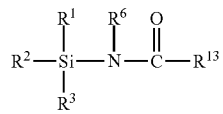

(1-4)

In the general formula (1-4), $R^1$, $R^2$ and $R^3$ are the same as those in the above-mentioned general formula (1-1). $R^6$ is the same as that in the above-mentioned general formula (1-2). $R^{13}$ represents a hydrogen atom, a saturated or unsaturated chain hydrocarbon group, a trifluoromethyl group, or a trialkylsilyl amino group.

When $R^{13}$ is a saturated or unsaturated chain hydrocarbon group, the saturated or unsaturated chain hydrocarbon group is the same as in the case where $R^4$ in the general formula (1-1) is a saturated or unsaturated chain hydrocarbon group.

When $R^{13}$ is a trialkylsilyl amino group, the alkyl group included in the trialkylsilyl amino group is the same as the alkyl group included in a trialkylsilyl group, a trialkylsiloxy group, or an alkoxy group in case where these groups are included in $R^{10}$ and $R^{11}$ in the general formula (1-3).

Specific examples of the silylating agent represented by the general formula (1-4) include N,N'-bis(trimethylsilyl)urea, N-trimethylsilyl acetamide, N-methyl-N-trimethylsilyl trifluoroacetamide, N,N-bis(trimethylsilyl)trifluoro acetamide, and the like.

Silylating agent represented by general formula (1-5)

[Chem. 5]

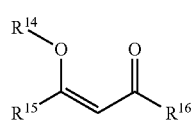

(1-5)

In the general formula (1-5), $R^{14}$ represents a trialkylsilyl group. $R^{15}$ and $R^{16}$, each independently represent a hydrogen atom or an organic group.

When $R^{14}$ is a trialkylsilyl group, the alkyl group included in the trialkylsilyl group is the same as the alkyl group included in a trialkylsilyl group, a trialkylsiloxy group, or an alkoxy group in case where these groups are included in $R^{10}$ and $R^{11}$ in the general formula (1-3).

When $R^{15}$ and $R^{16}$ are an organic group, the organic group is the same as the organic group in the case where $R^1$, $R^2$ and $R^3$ in the general formula (1-1) are an organic group.

Specific examples of the silylating agent represented by the general formula (1-5) include 2-trimethylsiloxypentane-2-ene-4-one and the like.

Silylating agent represented by general formula (1-6)

[Chem. 6]

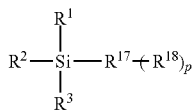
(1-6)

In the general formula (1-6), $R^1$, $R^2$ and $R^3$ are the same as those in the above-mentioned general formula (1-1). $R^1$ represents a saturated or unsaturated chain hydrocarbon group, a saturated or unsaturated non-aromatic cyclic hydrocarbon group, or a non-aromatic heterocyclic group. $R^{18}$ represents —$SiR^1R^2R^3$. p is 0 or 1.

When p is 0, the saturated or unsaturated chain hydrocarbon group, the saturated or unsaturated non-aromatic cyclic hydrocarbon group, or the non-aromatic heterocyclic group as $R^{17}$ is the same as $R^5$ in the general formula (1-1). When p is 1, the organic group as $R^{17}$ is a divalent group in which one hydrogen atom is removed from an organic group in a case where $R^1$, $R^2$ and $R^3$ in the general formula (1-1) are an organic group.

Specific examples of the silylating agent represented by the general formula (1-6) may include 1,2-bis(dimethylchlorosilyl)ethane, t-butyl dimethylchlorosilane, and the like.

Silylating agent represented by the general formula (1-7)

(1-7)

In the general formula (1-7), $R^{19}$ each independently represents a chain hydrocarbon group having 1 to 18 carbon atoms in which some or all of the hydrogen atoms may be substituted with a fluorine atom. q represents 1 or 2.

In the general formula (1-7), the number of carbon atoms of $R^{19}$ is preferably 2 to 18 and more preferably 8 to 18.

When a saturated chain hydrocarbon group in which $R^{19}$ is not substituted with a fluorine atom, examples thereof may include a methyl group, an ethyl group, an n-propyl group, an isopropyl group, a butyl group, a sec-butyl group, a tert-butyl group, an isobutyl group, an amyl group, an isoamyl group, a tert-amyl group, a hexyl group, a 2-hexyl group, a 3-hexyl group, a heptyl group, a 2-heptyl group, a 3-heptyl group, an isoheptyl group, a tert-heptyl group, an n-octyl group, an isooctyl group, a tert-octyl group, a 2-ethyl hexyl group, a nonyl group, an isononyl group, a decyl group, a dodecyl group, an tridecyl group, a tetradecyl group, a pentadecyl group, a hexadecyl group, a heptadecyl group, an octadecyl group, and the like.

In the case of an unsaturated chain hydrocarbon group in which $R^{19}$ is not substituted with a fluorine atom, examples thereof may include a vinyl group, a 1-propenyl group, an allyl group, an isopropenyl group, a 1-butenyl group, a 2-butenyl group, a 3-butenyl group, a 1,3-butadienyl group, a 1-ethyl vinyl group, a 1-methyl-1-propenyl group, a 1-methyl-2-propenyl group, a 4-pentenyl group, a 1,3-pentadienyl group, a 2,4-pentadienyl group, a 3-methyl-1-butenyl group, a 5-hexenyl group, a 2,4-hexadienyl group, a 6-heptenyl group, a 7-octenyl group, an 8-nonenyl group, a 9-decenyl group, a 10-undecenyl group, a 11-dodecenyl group, a 12-tridecenyl group, a 13-tetradecenyl group, a 14-pentadecenyl group, a 15-hexadecenyl group, a 16-heptadecenyl group, a 17-octadecenyl group, an ethynyl group, a propargyl group, a 1-propynyl group, a 1-butynyl group, a 2-butynyl group, a 3-butynyl group, a 1-pentynyl group, a 2-pentynyl group, a 3-pentynyl group, a 4-pentynyl group, a 1-hexynyl group, a 2-hexynyl group, a 3-hexynyl group, a 4-hexynyl group, a 5-hexynyl group, a 6-heptynyl group, a 7-octynyl group, a 8-nonynyl group, a 9-decynyl group, a 10-undecynyl group, a 11-dodecynyl group, a 12-tridecynyl group, a 13-tetradecynyl group, a 14-pentadecynyl group, a 15-hexadecynyl group, a 16-heptadecynyl group, a 17-octadecynyl group, and the like.

In the case of a chain hydrocarbon group in which $R^{19}$ is substituted with a fluorine atom, the number and site of the substitution of the fluorine atom are not particularly limited. The number of the substitution of the fluorine atom in the chain hydrocarbon group is preferably 50% or more, more preferably 70% or more, and particularly preferably 80% or more of the number of the hydrogen atoms included in the chain hydrocarbon group.

$R^{19}$ is preferably a linear chain hydrocarbon group having 1 to 18 carbon atoms in which some or all of the hydrogen atoms may be substituted with a fluorine atom, because excellent hydrophobization effect can be easily obtained. In addition, $R^{19}$ is preferably a saturated linear chain hydrocarbon group having 1 to 18 carbon atoms (an alkyl group having 1 to 18 carbon atoms), in which some or all of the hydrogen atoms may be substituted with a fluorine atom, from the viewpoint of the storage stability of the silylating agent.

In the general formula (1-7), q is 1 or 2, and preferably 1.

Silylating agent represented by general formula (1-8)

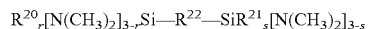
(1-8)

In the general formula (1-8), $R^{20}$ and $R^{21}$ each independently represent a hydrogen atom, or a linear or branched alkyl group having 1 to 4 carbon atoms. $R^{22}$ represents a linear or branched alkylene group having 1 to 16 carbon atoms. r and s each independently represent an integer of from 0 to 2.

$R^{20}$ and $R^{21}$ may be the same as or different form each other. $R^{20}$ and $R^{21}$ are preferably a hydrogen atom or a linear or branched alkyl group having 1 to 3 carbon atoms, more preferably a hydrogen atom or a methyl group, and particularly preferably a methyl group.

When $R^{20}$ and $R^{21}$ are a linear or branched alkyl group having 1 to 4 carbon atoms, specific examples thereof may include a methyl group, an ethyl group, an n-propyl group, an isopropyl group, an n-butyl group, a sec-butyl group, a tert-butyl group and an isobutyl group.

The compound represented by the general formula (1-8) includes a linear or branched alkylene group having 1 to 16 carbon atoms as $R^{22}$. The linear or branched alkylene group that is $R^{22}$ has preferably 1 to 10 carbon atoms, and more preferably 2 to 8 carbon atoms. Note here that the linear chain alkylene group is a methylene group or an α, ω-linear chain alkylene group, and the branched alkylene group is a methylene group and an alkylene group other than an α,ω-linear chain alkylene group. $R^{22}$ is preferably the linear chain alkylene group.

When $R^{22}$ is a linear or branched alkylene group having 1 to 16 carbon atoms, examples thereof may include a methylene group, a 1,2-ethylene group, a 1,1-ethylene group, a propane-1,3-diyl group, a propane-1,2-diyl group, a propane-1,1-diyl group, a propane-2,2-diyl group, a butane-1,4-diyl group, a butane-1,3-diyl group, a butane-1,2-diyl group, a butane-1,1-diyl group, a butane-2,2-diyl group, a butane-2,3-diyl group, a pentane-1,5-diyl group, a pentane-1,4-diyl group, a hexane-1,6-diyl group, a heptane-1,7-diyl group, an octane-1,8-diyl group, a 2-ethyl hexane-1,6-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, and the like.

In the compound represented by the general formula (1-8), s and r each independently are an integer of from 0 to 2. Since the synthesis and obtaining of the compound represented by the formula (1-8) are easy, s and r are preferably 1 or 2, and more preferably 2.

(Cyclic Silazane Compound)

As a silylating agent, a cyclic silazane compound is also preferable. Hereinafter, the cyclic silazane compound will be described.

Examples of the cyclic silazane compound may include cyclic disilazane compounds such as 2,2,5,5-tetramethyl-2,5-disila-1-azacyclopentane and 2,2,6,6-tetramethyl-2,6-disila-1-azacyclohexane; cyclic trisilazane compounds such as 2,2,4,4,6,6-hexamethylcyclotrisilazane and 2,4,6-trimethyl-2,4,6-trivinylcyclotrisilazane; cyclic tetrasilazane compounds such as 2,2,4,4,6,6,8,8-octamethylcyclotetrasilazane; and the like.

Among them, the cyclic disilazane compounds are preferable, and 2,2,5,5-tetramethyl-2,5-disila-1-azacyclopentane and 2,2,6,6-tetramethyl-2,6-disila-1-azacyclohexane are more preferable. The cyclic disilazane compounds include a 5-membered ring structure such as 2,2,5,5-tetramethyl-2,5-disila-1-azacyclopentane, and a 6-membered ring structure such as 2,2,6,6-tetramethyl-2,6-disila-1-azacyclohexane. The 5-membered ring structure is more preferable.

[Other Components in Silylating Agent Liquid]

The silylating agent liquid to be used in the present invention may contain components other than the above-mentioned silylating agents within a range where the objects of the present invention are not impaired. The other components are not particularly limited. Examples thereof include an organic solvent or the like. When the silylating agent is not liquid, an organic solvent is preferably contained. However, an organic solvent may not be contained if the silylating agent can be exposed onto the substrate surface.

The organic solvent that can be contained in the silylating agent liquid is not particularly limited, but an organic solvent that does not have a functional group reacting with a silylating agent is preferable. Organic solvents may be used singly or in a combination of two or more thereof.

Preferable organic solvents specifically may include sulfoxides such as dimethyl sulfoxide; sulfones such as dimethyl sulfone, diethyl sulfone, bis(2-hydroxyethyl)sulfone, and tetramethylene sulfone; amides such as N,N-dimethylformamide, N-methyl formamide, N,N-dimethyl acetamide, N-methyl acetamide, and N,N-diethyl acetamide; lactams such as N-methyl-2-pyrrolidone, N-ethyl-2-pyrrolidone, N-propyl-2-pyrrolidone, N-hydroxymethyl-2-pyrrolidone, and N-hydroxyethyl-2-pyrrolidone; imidazolidinones such as 1,3-dimethyl-2-imidazolidinone, 1,3-diethyl-2-imidazolidinone, and 1,3-diisopropyl-2-imidazolidinone; dialkyl glycol ethers such as dimethyl glycol, dimethyl diglycol, dimethyl triglycol, methyl ethyl diglycol, and diethyl glycol; (poly)alkylene glycol monoalkyl ethers such as ethylene glycol monomethyl ether, ethylene glycol monoethyl ether, ethylene glycol mono-n-propyl ether, ethylene glycol mono-n-butyl ether, diethylene glycol monomethyl ether, diethylene glycol monoethyl ether, diethylene glycol mono-n-propyl ether, diethylene glycol mono-n-butyl ether, triethylene glycol monomethyl ether, triethylene glycol monoethyl ether, propylene glycol monomethyl ether, propylene glycol monoethyl ether, propylene glycol mono-n-propyl ether, propylene glycol mono-n-butyl ether, dipropylene glycol monomethyl ether, dipropylene glycol monoethyl ether, dipropylene glycol mono-n-propyl ether, dipropylene glycol mono-n-butyl ether, tripropylene glycol monomethyl ether, and tripropylene glycol monoethyl ether; (poly)alkylene glycol monoalkyl ether acetates such as ethylene glycol monomethyl ether acetate, ethylene glycol monoethyl ether acetate, diethylene glycol monomethyl ether acetate, diethylene glycol monoethyl ether acetate, propylene glycol monomethyl ether acetate, and propylene glycol monoethyl ether acetate; the other ethers such as dimethyl ether, diethyl ether, methyl ethyl ether, dipropyl ether, diisopropyl ether, dibutyl ether, diisoamyl ether, diethylene glycol dimethyl ether, diethylene glycol methyl ethyl ether, diethylene glycol diethyl ether, and tetrahydrofuran; ketones such as methyl ethyl ketone, cyclohexanone, 2-heptanone, and 3-heptanone; alkyl lactate esters such as 2-hydroxy methyl propionate, and 2-hydroxy ethyl propionate; other esters such as 2-hydroxy-2-methyl ethyl propionate, 3-methoxy methyl propionate, 3-methoxy ethyl propionate, 3-ethoxy methyl propionate, 3-ethoxy ethyl propionate, ethoxy ethyl acetate, hydroxy ethyl acetate, 2-hydroxy-3-methylbutanoic acid methyl, 3-methyl-3-methoxybutyl acetate, 3-methyl-3-methoxybutyl propionate, ethyl acetate, n-propyl acetate, i-propyl acetate, n-butyl acetate, i-butyl acetate, n-pentyl formate, i-pentyl acetate, n-butyl propionate, ethyl butyrate, n-propyl butyrate, i-propyl butyrate, n-butyl butyrate, methyl pyruvate, ethyl pyruvate, n-propyl pyruvate, methyl acetoacetate, ethyl acetoacetate, and 2-ethyl oxobutanoate; lactones such as β-propiolactone, γ-butyrolactone, and δ-pentirolactone; linear chain, branched, or cyclic hydrocarbons such as n-hexane, n-heptane, n-octane, n-nonane, methyl octane, n-decane, n-undecane, n-dodecane, 2,2,4,6,6-pentamethyl heptane, 2,2,4,4,6,8,8-heptamethyl nonane, cyclohexane, and methyl cyclohexane; aromatic hydrocarbons such as benzene, toluene, naphthalene, and 1,3,5-trimethyl benzene; terpenes such as p-menthane, diphenyl menthane, limonene, terpinene, bornane, norbornane, and pinane; and the like. The organic solvents may be used singly or in a combination of two or more thereof. Among them, propylene glycol monomethyl ether acetate (PEMEA); linear and branched chain or circular hydrocarbon; terpenes such as p-menthane, diphenyl menthane, limonene, terpinene, bornane, norbornane, and pinane, are preferable.

In a silylating agent liquid (treated silylating agent liquid) obtained by the purification method according to the first or second aspect or the method for producing according to the third aspect, the concentration of the metal impurity can be reduced as mentioned above. Therefore, the silylating agent liquid can suitably be used as a substrate surface treatment liquid. In particular, it is suitable as a substrate surface treatment liquid to be used for producing a semiconductor device and the like.

<Film Forming Material>

The film forming material as an object to be purified preferably includes a silicon compound capable of producing a silanol group by hydrolysis. It is more preferable that the silicon compound is a silicon compound represented by the following general formula (2) or (3). The silicon compound represented by the following general formula (2) or (3) has high activity particularly with respect to hydrolysis, in heating or burning in formation of a film on a surface of the substrate, the temperature can be made lower than that of a conventional film forming material, and a film can be formed on a substrate surface without carrying out heat treatment.

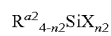  (2)

(In the general formula (2), $R^{a2}$ is a hydrogen atom or a monovalent hydrocarbon group. X is a group selected from the group consisting of a linear or branched alkoxy group having 1 to 5 carbon atoms, an isocyanate group, and a halogen atom.

n2 is an integer of 1 to 4.)

In the formula (2), X is preferably an isocyanate group, and n2 is preferably 4.

 (3)

(In the formula (3), $R^{a3}$ is a hydrogen atom or a monovalent hydrocarbon group, and n3 is 2 to 4.)

The above-mentioned silicon compounds may be used singly or in a combination of two or more thereof.

$R^{a3}$ in the formula (3) is a hydrogen atom or a monovalent hydrocarbon group. The hydrocarbon group as $R^{a3}$ is not particularly limited within a range where the objects of the present invention are not impaired, and an aliphatic hydrocarbon group having 1 to 12 carbon atoms is preferable.

Suitable examples of the aliphatic hydrocarbon group having 1 to 12 carbon atoms may include a methyl group, an ethyl group, an n-propyl group, an isopropyl group, an n-butyl group, a sec-butyl group, an isobutyl group, a tert-butyl group, an n-pentyl group, an isopentyl group, a neopentyl group, a cyclo pentyl group, an n-hexyl group, a cyclohexyl group, an n-heptyl group, an n-cycloheptyl group, an n-octyl group, an n-cyclooctyl group, an n-nonyl group, an n-decyl group, an n-undecyl group, and an n-dodecyl group. An aliphatic hydrocarbon group having 1 to 5 carbon atoms is more preferable.

Among the above-described hydrocarbon groups, a methyl group and an ethyl group are further preferable, and a methyl group is particularly preferable.

Among the silicon compounds represented by the general formula (3), tetraisocyanate silane, methyl triisocyanate silane, and ethyl triisocyanate silane are preferable.

The content of the silicon compound in the film forming material is not particularly limited as long as uniformly dissolved film forming materials can be prepared. The content of the silicon compound in the film forming material is preferably 0.01 to 50% by mass, more preferably 0.01 to 10% by mass, further preferably 0.01 to 5% by mass, and particularly preferably 0.01 to 1% by mass. When the silicon compound is contained in such a content, film coating can tend to be carried out more conformally.

The film forming material may contain any metal alkoxide from the viewpoint of formation property of a film. One type of metal alkoxide may be used, or a plurality of types of metal alkoxide can be used simultaneously. The content of metal alkoxide is not particularly limited, and it is preferably 0.01 to 20% by mass, more preferably 0.01 to 5% by mass, further preferably 0.01 to 1% by mass, and most preferably 0.1 to 0.5% by mass. When the film forming material contains metal alkoxide in such a content, the strength of the formed membrane tends to be improved. Furthermore, containing metal alkoxide can bring various property. For example, optical characteristics such as refractive index, solubility with respect to acids or base, or the like, can be changed.

(Organic Solvent)

The above-mentioned film forming material may further include an organic solvent. Specific examples of the solvent include organic solvents described above as specific examples and preferable examples of the organic solvents that can be contained in a silylating agent liquid. The organic solvent may be used singly and two or more thereof may be used in combination.

The content of the organic solvent in the film forming material is usually the remaining amount with respect to the total amount of the content of the silicon compound, the content of the metal alkoxide, and the contents of the other components to be described below.

[Other Components in Film Forming Material]

The film forming material may include various additives along with the silicon compound and metal alkoxide mentioned above within a range where the objects of the present invention are not impaired. Examples of the additives may include a surfactant, a viscosity regulator, an anti-foaming agent, and the like.

The film forming material is prepared by uniformly mixing and dissolving the above-described silicon compound, and if necessary, other components. A film forming material obtained by the purification method according to the first or second aspect or the method for producing according to the third aspect is preferably a monolayer molecular film forming material. When a film forming material obtained by the purification method according to the first or second aspect or the method for producing according to the third aspect is used, a film such as a $SiO_2$ film can be easily formed on the surface of the substrate by hydrolysis condensation of the silicon compound.

Furthermore, as a secondary effect caused by the use of the film forming material obtained by the purification method according to the first or second aspect or the method for producing according to the third aspect, it may be exemplified that a film of a metal oxide that has abundant hydroxyl groups can be formed regardless of the quality of the materials of the substrate. For example, in some cases, it may be difficult to modify the surfaces of a tungsten substrate, a titan nitride substrate, a silicon nitride substrate, a copper substrate, a gold substrate, and the like, by a silylating agent in the conventional known methods. However, before performing the treatment of the silylating agent, when a film of a metal oxide that has abundant hydroxyl groups is formed on a surface of a substrate by using the film forming material according to the present invention, the hydroxyl groups exposed on the surface of the film may be favorably reacted with the silylating agent. In that way, even when it is difficult to modify the surface with the silylating agent, the surface of the substrate is favorably modified.

<<Method for Forming Film>>

The method for forming a film on a surface of a substrate using the above-described film forming material is not particularly limited. Hereinafter, the method for forming a film will be described.

The material of a substrate on which a film is to be formed is not particularly limited, and the substrate may be selected from various inorganic substrates and organic substrates. In particular, when surface treatment is performed with a silylating agent after forming a film on a surface of a substrate using the above-described film forming material, modification of the surface may be favorably performed even with respect to substrates such as a tungsten substrate, a titan nitride substrate, a silicon nitride substrate, a copper substrate, a gold substrate, and the like, whose surfaces have been difficult to be modified using conventional known methods.

The method for forming a film on a surface of a substrate using a film forming material is not particularly limited as long as the film forming material can be applied onto the surface of the substrate and a hydrolysis reaction of the silicon compound can be performed on the surface of the substrate.

The method for applying a film forming material onto the surface of a substrate is not particularly limited. When the silicon compound is used as a solution, the amount of the silicon compound applied onto the surface of the substrate may be easily adjusted by adjusting the thickness of the coating film to be formed.

As for the treatment of the surface of the substrate by the film forming material, the film may be formed on the surface of the substrate by hydrolysis condensation of the silicon compound, but when the above-described film is formed, it is preferable that the surface of the substrate in a non-treated state be hydrophilized. Whether or not the surface of the substrate is hydrophilized can be determined by measuring the degree of hydrophilicity on the surface of the substrate in a known technique, for example, the measurement of the contact angle of water before and after the treatment of the surface of the substrate. By determining the hydrophilization on the surface of the substrate, it can be determined that the hydroxyl groups are plentifully introduced to some degree by the formation of a film on the surface of the substrate. When a large number of the hydroxyl groups are introduced into the surface of the substrate, the silylating agent is easily bound to the surface of the film that is formed by the condensation of the silicon compound.

Furthermore, the formation of the film composed of an inorganic oxide on the surface of the substrate can be determined by, for example, spin-coating the film forming material in a solution state on the substrate of the desired material. Specifically, the film is formed by applying the film forming material on the substrate in the air, rotating the substrate to uniformly apply the film forming material on the substrate, and then, spin-drying to blow the solvent. At this time, the moisture in the air and the silicon compound such as $Si(NCO)_4$ are subjected to a hydrolysis reaction, and then, subjected to condensation polymerization to form a film composed of an inorganic oxide. The thickness of the film composed of an inorganic oxide depends on the concentration of the silicon compound, the rotation speed at the time of being spin-applied, humidity, and the like. Presence and a thickness of the film formed by the above-mentioned method can be determined by, for example, an ellipsometer, nano-specification, and the like.

A method for applying a film forming material on the surface of a substrate is not particularly limited, and the known applying methods can be applied. Examples of the preferred applying methods may include a spraying method, a spin-coating method, a dip-coating method, a roll-coating method, and the like.

Note here that before the treatment with the film forming material, a natural oxidation film may be removed from the surface of the substrate when using the substrate having the natural oxidation film on the surface of the substrate such as a tungsten substrate and a copper substrate.

The film formed on the surface of a substrate using a film forming material by the above-described method has various excellent properties such as high etching resistance and high reactivity with a surface treating agent such as a silylating agent.

(Flattened Film)

A film forming material obtained by the purification method according to the first or second aspect or the method for producing according to the third aspect can be used for forming a flattened film. Since the film forming material obtained by the purification method according to the first or second aspect or the method for producing according to the third aspect contains a silicon compound having autoreactivity, the burning temperature when a film is formed can be made lower than that of a composition for forming a conventional silica-based film. Therefore, the above-mentioned film forming material is particularly suitable as a film forming material for forming a flattened film which is not preferably subjected to high-temperature burning.

(Insulating Film)

A film forming material obtained by the purification method according to the first or second aspect or the method for producing according to the third aspect contains the above-mentioned silicon compound and thereby can form an insulating film.

(Resin Layer for Imprinting)

A film forming material obtained by the purification method according to the first or second aspect or the method for producing according to the third aspect can be used as a resin layer for imprinting. Furthermore, the film forming material obtained by the purification method according to the first or second aspect or the method for producing according to the third aspect enables finer patterns to be transferred with high accuracy and conformal fine patterns to be formed, and, therefore, the film forming material can be used for forming a resin layer for imprinting at room temperature.

(Etching Mask)

A film forming material obtained by the purification method according to the first or second aspect or the method for producing according to the third aspect can be used for forming an etching mask. The film forming material obtained by the purification method according to the first or second aspect or the method for producing according to the third aspect has a compound having autoreactivity, and has a burning temperature for forming a film lower than that of a conventional silica-based composition, and therefore, the film forming material can be suitably used as a composition for forming an etching mask.

A film forming material obtained by the purification method according to the first or second aspect or the method for producing according to the third aspect is subjected to pattern formation using printing methods such as an inkjet printing method and a screen printing. The formed patterns can be used as a mask for etching. Furthermore, a pattern such as resist pattern whose surface is covered with a composition of the present invention can be used as a mask for etching. A surface of patterns such as resist pattern is covered with the film forming material of the present invention, and the upper part of the pattern is etched, thus enabling double patterns to be formed.

(High Refractive Film)

A film forming material obtained by the purification method according to the first or second aspect or the method for producing according to the third aspect can be used for forming a high refractive film. The film forming material of the present invention is embedded into the groove portions or hole portions, and the like, previously formed in optical elements such as a photoelectric integrated circuit, a photo integrated circuit, a CCD sensor, and a CMOS sensor, and the surface is processed by etching and the like, an optical guided wave path having a high refractive index can be formed.

In this way, the film forming material obtained by the purification method according to the first or second aspect or the method for producing according to the third aspect is excellent in coating characteristics or strength, and therefore can be suitably used for pattern formation by lithography, and formation of a flattened film, an insulating film, a high refractive film, a resin layer for imprinting or an etching mask, or the like.

<Diffusing Agent Composition that is Used for Diffusing Dopant into Semiconductor Substrate>

The diffusing agent composition includes a dopant (impurity diffusing component), and is used for diffusing a dopant into a semiconductor substrate. The diffusing agent composition as an object to be purified preferably includes a silicon compound capable of producing a silanol group by hydrolysis represented by the above general formula (2). It is more preferable that the above-mentioned silicon compound is a silicon compound represented by the following general formula (4). When a diffusing agent composition is applied to a semiconductor substrate to form a thin film, the silane compound is hydrolysis-condensed, and a very thin silicon-oxide film is formed in the coated film. When a very thin silicon-oxide film is formed in the coated film, diffusion of a dopant to the outside of the substrate is suppressed, even if a film made of a diffusing agent composition is a thin film, the dopant can be diffused into a semiconductor substrate excellently and uniformly.

$$R^{a4}_{4-n4}Si(NCO)_{n4} \quad (4)$$

(In the formula (4), $R^{a4}$ is a hydrocarbon group, and n4 is an integer of 3 or 4.)

A hydrocarbon group as $R^{a4}$ in the formula (4) is not particularly limited within a range where the objects of the present invention are not impaired. As $R^{a4}$, an aliphatic hydrocarbon group having 1 to 12 carbon atoms, an aromatic hydrocarbon group having 1 to 12 carbon atoms, and an aralkyl group having 1 to 12 carbon atoms are preferable.

Suitable examples of the aliphatic hydrocarbon group having 1 to 12 carbon atoms include a methyl group, an ethyl group, an n-propyl group, an isopropyl group, an n-butyl group, a sec-butyl group, an isobutyl group, a tert-butyl group, an n-pentyl group, an isopentyl group, a neopentyl group, a cyclopentyl group, an n-hexyl group, a cyclohexyl group, an n-heptyl group, an n-cycloheptyl group, an n-octyl group, an n-cyclooctyl group, an n-nonyl group, an n-decyl group, an n-undecyl group, and an n-dodecyl group.

Suitable examples of the aromatic hydrocarbon group having 1 to 12 carbon atoms include a phenyl group, a 2-methyl phenyl group, a 3-methyl phenyl group, a 4-methyl phenyl group, a 2-ethyl phenyl group, a 3-ethyl phenyl group, a 4-ethyl phenyl group, an α-naphthyl group, a β-naphthyl group, and a biphenylyl group.

Suitable examples of the aralkyl group having 1 to 12 carbon atoms include a benzyl group, a phenethyl group, an α-naphthyl methyl group, a β-naphthyl methyl group, a 2-α-naphthyl ethyl group, and a 2-β-naphthyl ethyl group.

Among the hydrocarbon groups described above, a methyl group and an ethyl group are preferable, and a methyl group is more preferable.

Among the compounds represented by the formula (4), tetraisocyanate silane, methyl triisocyanate silane, and ethyl triisocyanate silane are preferable and tetraisocyanate silane is more preferable.

[Dopant]

A dopant (an impurity diffusing component) is not particularly limited as long as it is a component that has conventionally been used for doping a semiconductor substrate, and it may be an n-type dopant or a p-type dopant. Examples of the n-type dopant include elemental substances such as phosphorus, arsenic, and antimony, as well as compounds including these elements. Examples of the p-type dopant include elemental substances such as boron, gallium, indium, and aluminum, as well as compounds including these elements.

As the dopant, from the viewpoint of easiness in availability and handling, a phosphorus compound, a boron compound, or an arsenic compound are preferable. Examples of preferable phosphorus compounds include phosphoric acid, phosphorous acid, diphosphorous acid, polyphosphoric acid, and diphosphorus pentaoxide, phosphorous acid esters, phosphoric acid esters, phosphorous acid tris(trialkylsilyl), phosphoric acid tris(trialkylsilyl), and the like. Examples of preferable boron compound include boric acid, metaboric acid, boronic acid, perboric acid, hypoboric acid, diboron trioxide, and boric acid trialkyl. Preferable examples of the arsenic compound include arsenic acid, and trialkyl arsenate.

Preferable examples of the phosphorus compounds include phosphorous acid esters, phosphoric acid esters, phosphorous acid tris(trialkylsilyl), and phosphoric acid tris(trialkylsilyl). Among them, trimethyl phosphate, triethyl phosphate, trimethyl phosphite, triethyl phosphite, phosphoric acid tris(trimethoxysilyl), and phosphorous acid tris(trimethoxysilyl) are preferable; trimethyl phosphate, trimethyl phosphite, and phosphoric acid tris(trimethylsilyl) are more preferable; and trimethyl phosphate is particularly preferable.

Preferable examples of the boron compound include trimethoxy boron, triethoxy boron, trimethyl boron, and triethyl boron.

Preferable examples of the arsenic compound include arsenic acid, triethoxy arsenic, and tri-n-butoxy arsenic.

The content of the dopant in the diffusing agent composition is not particularly limited. The content of the dopant in the diffusing agent composition is set such that the amount (mol) of elements, which act as a dopant in a semiconductor substrate, such as phosphorus, arsenic, antimony, boron, gallium, indium, and aluminum, included in the dopant, is preferably 0.01 to 5 times and more preferably 0.05 to 3 times as the mol number of Si included in the silicon compound.

The content of the silicon compound in the diffusing agent composition is preferably 0.001 to 3.0% by mass, and more preferably 0.01 to 1.0% by mass as a concentration of Si. When the diffusing agent composition contains the silicon compound in such a concentration, diffusion of the dopant from a thin coating film formed using the diffusing agent composition to the outside is excellently suppressed. Thus, a dopant can be efficiently and uniformly diffused into a semiconductor substrate. From the viewpoint of preventing a dopant from being removed as impurities to be removed in the purification method of the present invention, it is preferable that an object to be purified does not include a dopant, and that a diffusing agent composition purified by the purification method of the present invention is allowed to contain a dopant.

(Organic Solvent)

A diffusing agent composition may further include an organic solvent. Specific examples of the solvent include an organic solvent mentioned above as specific examples and preferable examples of the organic solvent that can be contained in a silylating agent liquid. The organic solvent may be used singly and two or more thereof may be used in combination. Furthermore, in a case where the diffusing agent composition includes a silicon compound, it is preferable that the diffusing agent does not substantially water. Not substantially containing water means that the diffusing agent composition does not contain water in such an amount that the silicon compound inhibits the objects of the present invention by hydrolysis.

[Other Components]

The diffusing agent composition may include various additives such as a surfactant, an anti-foaming agent, a pH-adjusting agent, a viscosity regulator, and the like, within a range where the objects of the present invention are not impaired. Furthermore, the diffusing agent composition may include a binder resin for the purpose of improving the coating characteristics and film formation property. As the binder resin, various resin can be used, and an acrylic resin is preferable.

<Polyimide and/or Polyamideimide Porous Membrane>

A polyimide and/or polyamideimide porous membrane used in a purification method for purifying a liquid as an object to be purified according to the first aspect has communicating pores. The communicating pores may have individual pores that impart porosity to the polyimide and/or polyamideimide porous membrane (hereinafter they may be abbreviated simply to "pores"), and the pores are preferably those having a curved inner surface to be described later, and are more preferably substantially spherical pores to be described later. In the polyimide and/or polyamideimide porous membrane, it is preferable that portions formed by adjacent individual pores become communicating pores, and the pores having a communicating structure are ordinarily connected to one another to form a flow path for a liquid to be purified, as a whole. The "flow path" is ordinarily formed by continuity of individual "pores" and/or "communicating pores". Individual pores can also be considered to be pores formed by removing individual fine particles present in a polyimide-based resin-fine particle composite membrane in a post process in a method for producing a polyimide-based resin porous membrane to be described later. Further, the communicating pores can also be considered to be adjacent individual pores formed by removing fine particles in a post process in portions where individual fine particles present in a polyimide-based resin-fine particle composite membrane are in contact with one another in the method for producing the polyimide-based porous membrane to be described later.

The above-mentioned polyimide and/or polyamideimide porous membrane preferably has communicating pores that ensure flow paths for allowing a fluid to pass through the porous membrane so that the communicating pores open to an external surface of the porous membrane are connected inside the porous membrane and are also open to an external surface of the other side (backside) of the porous membrane. The presence of communicating pores in the polyimide and/or polyamideimide porous membrane of the present invention can be expressed, for example, by Gurley air permeability, and the Gurley air permeability may be, for example, 30 to 1000 sec.

The Gurley air permeability of the polyimide and/or polyamideimide porous membrane may be, for example, 1000 sec or less, preferably 600 sec or less, still more preferably 500 sec or less, most preferably 300 sec or less. The lower the Gurley air permeability, the better the results. Thus, the lower limit of the Gurley air permeability is not determined, in particular. Preferably, however, from the viewpoint of efficiently performing treatment such as metal removal while maintaining the flow rate of a fluid passing through the polyimide and/or polyamideimide porous membrane, the Gurley air permeability is, for example, 30 sec or more. When the Gurley air permeability is 1000 sec or less, the porosity is satisfactorily high and, thus, in the present invention, the effect of purifying the liquid can be enhanced.

The above-mentioned polyimide and/or polyamideimide porous membrane preferably includes communicating pores having a pore diameter of 1 to 200 nm. The pore diameter of the communicating pores is preferably 3 to 180 nm, more preferably 5 to 150 nm, and still more preferably 10 to 130 nm. Such a pore diameter of the communicating pores is the diameter of the communicating pores. One communicating pore is ordinarily formed by two adjacent particles by a producing method to be described later. Accordingly, the diameter may be a diameter in a direction perpendicular to a longitudinal direction when the longitudinal direction is defined as a direction in which two pores constituting the communicating pores are continuous. Regarding the pore diameter of the communicating pores, the broader the distribution of the pore diameters of individual pores that impart porosity to the polyimide and/or polyamideimide porous membrane, the smaller the diameter of the communicating pores per se formed by adjacent individual pores tends to be. Further, from the viewpoint of reducing the pore diameter of the communicating pores, the porosity of the porous membrane may be for example, approximately in the range of 60 to 90%, preferably 60 to 80%, more preferably 70%. Further, also when an imide bond ring-opening step to be described later is not carried out, the pore diameter of the communicating pores tends to be reduced.

The above-mentioned polyimide and/or polyamideimide porous membrane has communicating pores and, thus, when a fluid is allowed to pass through the porous membrane, the fluid can pass through the inside of the porous membrane. The polyimide and/or polyamideimide porous membrane preferably internally has a flow path composed of communicating pores in continuity which connect individual pores each having a curved inner surface. Accordingly, it is considered that the fluid can be passed through the inside of the porous membrane and, further, be passed through while it is brought into contact with the curved surface of the individual pores, leading to an increased area of contact with the inner surface of the pores that allows minute substances such as metal particles present in the fluid to be easily adsorbed on the pores in the porous membrane.

As described above, the above-mentioned polyimide and/or polyamideimide porous membrane is a porous membrane containing pores having a curved inner surface, and, more preferably, most of (preferably substantially all of) the pores in the porous membrane have a curved inner surface. In the present specification, "having a curved inner surface" with respect to the pore means that at least the inner surface of pores forming porosity has a curved surface in at least part of the inner surface.

It is preferable that substantially all of at least the inner surfaces of the pores in the above-mentioned porous membrane are curved surfaces. These pores may be referred to as "substantially spherical pores". In the present specification, the "substantially spherical pores" means the pores having an inner surface that forms a substantially spherical space. Preferably, the substantially spherical pores can also be considered to be pores formed when fine particles used in the method for producing a polyimide-based resin porous membrane to be described later is substantially spherical. In the present specification, the "substantially spherical" is a concept including a completely spherical form but is not necessarily limited to the completely spherical form and is a concept including a substantially spherical form. In the present specification, the "substantially spherical" means that the sphericity defined by a value obtained by dividing the major axis of a particle by the minor axis of the particle is within 1±0.3. The substantially spherical pores of the polyimide and/or polyamideimide porous membrane of the present invention preferably have sphericity within 1±0.1, and more preferably within 1±0.05.

When the pores in the porous membrane have a curved inner surface, it can be considered that there is a possibility that, when a fluid is allowed to pass into the above-mentioned polyimide and/or polyamideimide porous membrane, the fluid is satisfactorily penetrated into the inside of the porous in the porous membrane and thus can be brought into satisfactory contact with the inner surface of the pores and, in some cases, convection occurs along the curved inner surface. Thus, it can be considered that minute substances such as metal particles present in the fluid are likely to be adsorbed in the recesses that may exist on the pores or the inner surface of the pores in the porous membrane of the present invention. The substantially spherical pores may have additional recesses in the inner surface. The recesses may be formed by pores having a smaller pore diameter than substantially spherical spheres having openings in the inner surface.

The polyimide and/or polyamideimide porous membrane of the present invention may be, for example, a porous membrane having an average pore diameter of 100 to 2000 nm, and the average pore diameter is preferably 200 to 1000 nm, more preferably 300 to 900 nm. In the present specification, for the porous membrane subjected to chemical etching treatment to be described later, the change amount in average size of the communicating pores is determined by a porometer, and an actual average pore diameter is determined from the value. On the other hand, for the polyamideimide porous membrane not subjected to the chemical etching, the average pore diameter of the fine particles used in producing the porous membrane can be regarded as the average pore diameter.

Preferably, the above-mentioned polyimide and/or polyamideimide porous membrane has a structure including substantially spherical pores that have an average spherical diameter of 50 to 2000 nm and are mutually connected to one another. The average spherical diameter of the substantially spherical pores is preferably 100 to 1000 nm, more preferably 200 to 800 nm. The average spherical diameter of the substantially spherical pores can be determined by the same method as described above in connection with the average pore diameter in the porous membrane.

The above-mentioned polyimide and/or polyamideimide porous membrane may be obtained as a porous membrane having a porosity of, for example, 50 to 90% by mass, and preferably 55 to 80% by mass, as determined by a method to be described later.

The polyimide and/or polyamideimide porous membrane used in the purification method for purifying a liquid as an object to be purified according to the first aspect contains a resin and may be substantially composed only of a resin. Specifically, the resin content is 95% by mass or more, preferably 98% by mass or more, and more preferably 99% by mass or more. Resins contained in the polyimide and/or polyamideimide porous membrane of the present invention are preferably polyimide and/or polyamideimide, more preferably polyimide-containing resins, and may be polyimide alone. In the present specification, the polyimide and/or polyamideimide may also be referred to as "polyimide-based resin".

The above-mentioned polyimide and/or polyamideimide contained in the polyimide and/or polyamideimide porous membrane (hereinafter it may be abbreviated to "polyimide-based resin porous membrane" or "porous membrane") may contain at least one selected from the group consisting of a carboxy group, a salt-type carboxy group, and an —NH— bond. Preferably, the polyimide and/or polyamideimide has a carboxy group, a salt-type carboxy group and/or an —NH— bond at a position other than the main chain terminal of the polyimide and/or polyamideimide.

In the present specification, the "salt-type carboxy group" means a group formed by substituting a hydrogen atom in the carboxy group with a cation component. In the present specification, the "cation component" may be a cation itself that is in a completely ionized state itself, or a cation constituent that is ionically bonded to —COO— and is in a state of virtually no charge, or alternatively may be a cationic constituent having a partial charge that is an intermediate state between both of them. In the case where the "cation component" is an M ion component of n-valent metal M, the cation itself is expressed by $M^{n+}$, and the cation constituent is expressed by "M" in "—$COOM_{1/n}$".

In the present specification, cations formed in ion dissociation of compounds described as compounds containing chemical etching solutions, to be described later, may be mentioned as the "cation component", and representative examples thereof include ion components or organic alkali ion components. For example, when the alkali metal ion component is a sodium ion component, the cation itself is sodium ion ($Na^+$); the cationic constituent is an element represented by "Na" in "—COONa"; and the cationic constituent having a partial charge is $Na^{b+}$. In the present invention, the cation component is not particularly limited, and any of inorganic components, organic components such as $NH_4^+$, $N(CH_3)_4^+$ and the like is possible. Examples of inorganic components include metal elements including alkali metals such as Li, Na, and K, alkaline earth metals including Mg and Ca. Organic components, particularly organic alkali ion components include $NH_4^+$, for example, quaternary ammonium cations represented by $NR_4^+$ wherein four R's may be the same or different and each represent an organic group. The organic group as above described R is preferably an alkyl group, more preferably an alkyl group having 1 to 6 carbon atoms. Examples of quaternary ammonium cations include $N(CH_3)_4^+$ and the like.

In the present specification, the state of the "salt-type carboxy group" and "cation component" is not particularly limited and may depend upon an environment where the polyimide and/or polyamideimide exists, for example, may be in an aqueous solution, in an organic solvent, in a dried state, or the like. When the cation component is a sodium ion component, for example, in an aqueous solution, there is a possibility that the component is dissociated into —COO— and $Na^+$, while, in an organic solvent or in a dried state, there is a high possibility that the component is not dissociated.

The above-mentioned polyimide and/or polyamideimide may have at least one selected from the group consisting of a carboxy group, a salt-type carboxy group and an —NH— bond. When at least one of these is contained, the polyimide and/or polyamideimide ordinarily has both the carboxyl group and/or the salt-type carboxy group and —NH— bond. In terms of the carboxy group and/or the salt-type carboxy group, the polyimide and/or polyamideimide may have only a carboxy group, may have only a salt-type carboxy group, or may have both a carboxy group and a salt type carboxy group. The ratio of the carboxy group to the salt-type carboxy group possessed by the polyimide and/or polyamideimide may vary depending upon, for example, an environment where the polyimide and/or polyamideimide exist, and also affected by the concentration of the cation component, even in identical polyimide and/or polyamideimide.

For the polyimide, the total number of moles of carboxy groups and salt-type carboxy groups in the above-mentioned polyimide and/or polyamideimide is usually equimolar to the —NH— bond, and in particular, in the method for producing a polyimide porous membrane, to be described later, when the carboxy group and/or the salt-type carboxy group is formed from part of an imide bond in the polyimide, —NH— bond is also formed substantially simultaneously, and the total number of moles of carboxy groups and salt-type carboxy groups is equimolar to the formed —NH— bond. For the polyamideimide, the total number of moles of carboxy groups and salt-type carboxy groups in polyamideimide is not necessarily equimolar to the —NH— bond, but depends on the conditions of an imide bond ring-opening step such as chemical etching to be described later.

The above-mentioned polyimide and/or polyamideimide may be one having at least one unit selected from the group consisting of constitutional units represented by the following formulae (3) to (6). The polyimide may include constitutional units represented by the following formula (3) and/or formula (4), and the polyamideimide may include constitutional units represented by the following formula (5) and/or (6).

[Chem. 7]

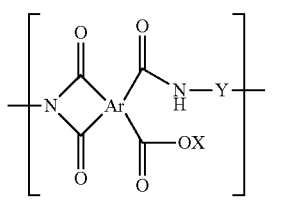
(3)

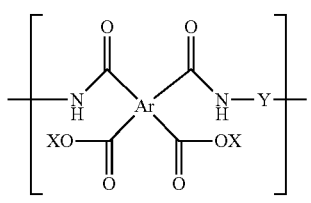
(4)

[Chem. 8]

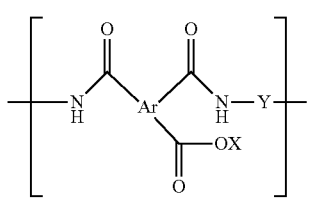
(5)

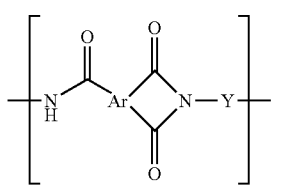
(6)

In the above formulae, X is the same or different and is a hydrogen atom or a cation component. Ar is an aryl group and may be the same as an aryl group represented by Ar to which the carbonyl group is bonded in a repeating unit represented by the formula (1) constituting the polyamide acid, to be described later, or a repeating unit represented by the formula (2) constituting the aromatic polyimide. Y is a divalent residue excluding the amino group of the diamine compound and may be the same as an aryl group represented by Ar to which N is bonded in a repeating unit represented by the formula (1) constituting the polyamide acid, to be described later, or a repeating unit represented by the formula (2) constituting the aromatic polyimide.

The above-mentioned polyimide and/or polyamideimide respectively may have a constituent unit represented by the formula (3) and/or the formula (4) for polyimides and a constituent unit represented by the formula (5) for polyamideimides formed as a result of the ring-opening of part of imide bond ([—C(=O)]$_2$—N—) possessed by general polyimides and/or polyamideimides. For the polyamideimide, however, the present inventors have found that the object of the present invention can also be attained by only having an amide bond (—NH—C(=O)—) originally possessed irrespective of the ring-opening of an imide bond possessed by a general polyamideimide. Also for the polyamideimide, however, the presence of a constituent unit represented by the formula (5) formed as a result of the ring-opening of part of imide bond originally possessed by the polyamideimide is preferable.

The above-mentioned polyimide and/or polyamideimide may be brought to a polyimide and/or polyamideimide porous membrane having at least one selected from the group consisting of a carboxy group, a salt-type carboxy group, and an —NH— bond by the ring-opening of part of the imide bond. The unconversion rate in the ring-opening of part of the imide bond is determined as follows.

(1) For the polyimide and/or polyamideimide porous membrane not subjected to an imide bond ring-opening process to be described later (provided that, when varnish for the preparation of the porous membrane contains a polyamide acid, an imidization reaction is regarded as having been substantially completed in a burning step), a value (X1) is determined by dividing the area of a peak representing the imide bond measured by the Fourier transform infrared spectroscopy (FT-IR) apparatus by the area of a peak representing benzene measured also by the FT-IR apparatus.

(2) Regarding the resultant polyimide and/or polyamideimide porous membrane, using the same polymer (varnish) as the porous membrane for which the value (X1) was determined, for the polyimide and/or polyamideimide porous membrane after the imide bond ring-opening step to be described later, a value (X2) is determined by dividing the area of a peak representing the imide bond measured by the Fourier transform infrared spectroscopy (FT-IR) apparatus by the area of a peak representing benzene measured also by the FT-IR apparatus.

(3) Unconversion rate (%)=(X2)÷(X1)×100

For the polyimide and/or polyamideimide porous membrane of the present invention, the unconversion rate is preferably 60% or more, more preferably 70% to 99.5%, and still more preferably 80 to 99%. A porous membrane containing polyamideimide includes an —NH— bond, and, thus, in this case, the unconversion rate may be 100%.

When the above-mentioned polyimide and/or polyamideimide porous membrane is a polyimide porous membrane, a value is determined as an imidization ratio by dividing the area of a peak representing the imide bond measured by Fourier transform infrared spectroscopy (FT-IR) apparatus by the area of a peak representing benzene measured by the FT-IR apparatus. For the polyimide, the X2 value as described above is preferably 1.2 or more, more preferably 1.2 to 2, still more preferably 1.3 to 1.6, even more preferably 1.30 to 1.55, particularly preferably 1.35 to less than 1.5. Further, in the present invention, the imidization ratio for X1 is preferably 1.5 or more. For the imidization ratio, the relatively larger the numeral, the greater the number of imide bonds, that is, the less the ring-opened imide bonds described above.

<Method for Producing Polyimide-Based Resin Porous Membrane>

The above-mentioned polyimide and/or polyamideimide porous membrane can be produced by a method including a step of forming a carboxy group and/or a salt-type carboxy group from part of an imide bond in polyimide and/or polyamideimide (hereinafter it may be referred to as "imide bond ring-opening step"). In the imide bond ring-opening step, as described above, when a carboxy group and/or a salt-type carboxy group is formed from part of the imide bond, theoretically, an —NH— bond equimolar to these groups is also substantially simultaneously formed. The imide bond ring-opening step is preferably carried out by chemical etching, to be described later.

However, when the resin contained in the polyimide and/or polyamideimide porous membrane is substantially composed of polyamideimide, the resin has already —NH— bond without imide bond ring-opening process, contributing favorable adsorption power. Accordingly, there is no particular need to decrease the flow rate of the fluid, and, thus, the imide bond ring-opening step is not always necessary. Preferably, however, the imide bond ring-opening step is carried out from the viewpoint of effectively attaining the object of the present invention.

The above-mentioned method for producing a polyimide and/or polyamideimide porous membrane may include a step of forming a carboxy group and/or a salt-type carboxy group from part of imide bonds in polyimide and/or polyamideimide (imide bond ring-opening step).

In the method for producing a polyimide and/or polyamideimide porous membrane, preferably, a molded membrane of a film or the like composed mainly of a polyimide and/or polyamideimide (which may be abbreviated to "polyimide and/or polyamideimide molded membrane") is prepared followed by the imide bond ring-opening step. The polyimide and/or polyamideimide molded membrane to be subjected to the imide bond ring-opening step may be porous or nonporous, and the shape thereof is not particularly limited. From the viewpoint of enhancing the porosity in the polyimide and/or polyamideimide porous membrane, preferably, the polyimide and/or polyamideimide molded membrane is porous and/or is preferably in the form of a thin shape such as a film.

As described above, the polyimide and/or polyamideimide molded membrane may be non-porous when subjected to the imide bond ring-opening step. In this case, preferably, pores are formed after the imide bond ring-opening step. A method of porous formation of the polyimide and/or polyamideimide molded membrane irrespective of whether it is before or after the imide bond ring-opening step is preferably a method including a fine particle removing step in which fine particles are removed from a composite membrane of a polyimide and/or a polyamideimide with fine particles (which may hereinafter be referred to as "polyimide-based resin-fine particle composite membrane") for the porous formation.

In the above-mentioned method for producing a polyimide and/or polyamideimide porous membrane, (a) before the fine particle removing step, the composite membrane of the polyimide and/or polyamideimide with the fine particles may be subjected to the imide bond ring-opening step, or alternatively, (b) after the fine particle removing step, the polyimide and/or polyamideimide molded membrane that has been rendered porous by the step may be subjected to the imide bond ring-opening step. However, the latter method (b) is preferred from the viewpoint of enhancing the porosity in the resultant polyimide and/or polyamideimide porous membrane.

The method for producing the polyimide and/or polyamideimide porous membrane of the present invention will be described in more detail by mainly taking the form of a membrane (a porous membrane) that is a preferred embodiment. The membrane can be suitably produced using a varnish.

[Manufacture of Varnish]

Varnish production is carried out by mixing an organic solvent containing fine particles previously dispersed therein with polyamide acid, polyimide or polyamideimide at any ratio, or by polymerizing tetracarboxylic acid dianhydride and diamine in an organic solvent containing fine particles previously dispersed therein to form a polyamide acid, or by further subjecting the polyamide acid to imidization to form a polyimide. And finally, the viscosity is preferably 300 to 2000 cP, more preferably 400 to 1800 cP. When viscosity of the varnish is in the above defined range, the film can be evenly formed.

In the varnish, in preparing a polyimide-based resin-fine particle membrane by burning (or drying when the burning is optional), fine particles of resin and polyamide acid or polyimide or polyamideimide may be mixed together so that the fine particle/polyimide-based resin ratio is 1 to 4 (mass ratio), and the fine particle/polyimide-based resin ratio is preferably 1.1 to 3.5 (mass ratio). Further, in preparing the polyimide-based resin-fine particle composite membrane, fine particles and polyamide acid or polyimide, or polyamideimide may be mixed together so that the fine particle/polyimide-based resin volume ratio is 1.1 to 5. Further, the fine particle/polyimide-based resin ratio is more preferably 1.1 to 4.5 (volume ratio). When the mass ratio or the volume ratio of the fine particle/polyimide-based resin is not less than the lower limit value, pores can have an appropriate density as the porous membrane. When mass ratio or the volume ratio of the fine particle/polyimide-based resin is not more than the upper limit value, the membrane can be stably formed without posing a problem of an increase in viscosity or cracking in the membrane. Note here that in the present specification, the volume % and the volume ratio are values at 25° C.

<Fine Particles>

The fine particles used in the present invention may be formed of any material without particular limitation as long as the material is insoluble in the organic solvent used in the varnish and can be selectively removed after the film formation. Examples of inorganic materials include metal oxides such as silica (silicon dioxide), titanium oxide, alumina ($Al_2O_3$), and calcium carbonate, and examples of organic materials include fine particles of organic polymers (resin fine particles) such as high molecular weight olefins (for example, polypropylene, polyethylene), polystyrenes, acrylic resins (resins of methyl methacrylate, isobutyl methacrylate, polymethyl methacrylate (PMMA), etc.), epoxy resins, celluloses, polyvinyl alcohols, polyvinyl butyrals, polyesters, polyethers, and polyethylenes.

Examples of inorganic materials in producing polyimide-based resin porous membranes can include silicas such as colloidal silica or PMMA that are fine particles of organic polymers. Among others, spherical particles are preferably selected from the viewpoint of forming very small pores having a curved inner surface.

Fine particles of resin mentioned above may be selected, for example, from ordinary linear polymers and well-known depolymerizable polymers according to purposes without particular limitation. The ordinary linear polymer is a polymer that undergoes random cleaving of molecular chains of the polymer in thermal decomposition, and the depolymerizable polymer is a polymer that is decomposed into monomers in thermal decomposition. Both polymers can be removed from the polyimide-based resin film by decomposing them into monomers, low molecular weight substances, or $CO_2$ at the time of heating. The decomposition temperature of the resin fine particles used is preferably 200 to 320° C., more preferably 230 to 260° C. When the decomposition temperature is 200° C. or more, the film can be formed even when a high boiling point solvent is used for the varnish, and the range of selection of burning conditions for the polyimide-based resin is widened. When the decomposition temperature is 320° C. or less, only the resin fine particles can be allowed to disappear without thermal damage to the polyimide-based resin.

Among these depolymerizable polymers, methyl methacrylate or isobutyl methacrylate alone (polymethyl methacrylate or polyisobutyl methacrylate) having a low thermal decomposition temperature alone or a copolymerized polymer containing them as a main component is preferable from the viewpoint of handling during pore formation.

The fine particles mentioned above are preferably those having a high sphericity ratio from the viewpoint of easy formation of curved inner surfaces in the resultant porous membrane. The particle diameter (average diameter) of the fine particles to be used may be, for example, 50 to 2000 nm, and preferably 200 to 1000 nm. Preferably, when a polyimide-based resin porous membrane obtained by removing fine particles is used as a separating material or an adsorbing material to allow a fluid to pass through, a fluid can be brought into full contact with the inner surface of the pores in the porous membrane, so that minute substances such as metal particles contained in the fluid can be efficiently adsorbed. The particle diameter distribution index (d25/75) may be from 1 to 6, preferably from 1.6 to 5, more preferably from 2 to 4. When the lower limit is 1.6 or more, particles can be efficiently filled in the inside of the membrane, and, thus, a flow channel is likely to be formed, advantageously contributing to improved flow rate. Further, it is considered that pores having a different size are formed, and the convection is changed, contributing to improved adsorption. Note here that d25 and d75 are the values of particle diameters of 25% and 75%, respectively, of the particle size distribution, and in this specification, d25 is the larger particle diameter.

Further, in the producing method to be described later, when the unburned composite membrane is formed as a two-layered unburned composite membrane, the fine particles (B1) used for the first varnish and the fine particles (B2) used for the second varnish may be the same or different. In order to make the pores on the side in contact with a base material denser, preferably, the fine particles of (B1) have smaller or the same particle size distribution index than the fine particles of (B2). Alternatively, preferably, the fine particles of (B1) have a smaller sphericity ratio than the fine particles of (B2) or are the same. Further, preferably, the fine particles of (B1) have smaller particle diameters (average diameters) of the fine particles than the fine particles of (B2). In particular, fine particles of (B1) having a diameter of 100 to 1000 nm (more preferably 100 to 600 nm) and fine particles of (B2) having a diameter of 500 to 2000 nm (more preferably 700 to 2000 nm) are preferred. When the diameter of the fine particles of (B1) is smaller than the diameter of the fine particles of (B2), the opening ratio of the pores on the surface of the obtained porous polyimide-based resin porous membrane can be made uniform and high; and the strength of the porous membrane (membrane) can be increased as compared with the case where the entirety of the porous polyimide-based resin porous membrane has the particle diameter of the fine particles of (B1).

In the present invention, in order to uniformly disperse the fine particles in the varnish, a dispersant may be further added together with the fine particles. The addition of the dispersant can allow polyamide acid, polyimide or polyamideimide to be more uniformly mixed with the fine particles, and fine particles in the molded or formed precursor film can be uniformly distributed. As a result, in order to provide dense openings in the surface of the finally obtained polyimide-based resin porous membrane and to improve the air permeability of the polyimide-based resin porous membrane, communicating pores through which the front and back surfaces of the porous membrane are efficiently communicating can be formed.

The dispersant used in the present invention is not particularly limited and well-known dispersants can be used. Examples of dispersants include, but are not limited to, anionic surfactants such as coconut fatty acid salts, castor sulfated oil salts, lauryl sulfate salts, polyoxyalkylene allyl phenyl ether sulfate salts, alkylbenzene sulfonic acids, alkyl benzene sulfonates, alkyl diphenyl ether disulfonates, alkyl naphthalene sulfonates, dialkyl sulfosuccinates, isopropyl phosphate, polyoxyethylene alkyl ether phosphate salts, polyoxyethylene allyl phenyl ether phosphate salts; cationic surfactants such as oleyl amine acetate, lauryl pyridinium chloride, cetyl pyridinium chloride, lauryl trimethyl ammonium chloride, stearyl trimethyl ammonium chloride, behenyltrimethylammonium chloride, didecyl dimethyl ammonium chloride; amphoteric surfactants such as cocoalkyldimethylamine oxide, fatty acid amidopropyldimethylamine oxide, alkylpolyaminoethylglycine hydrochloride, amidobetaine type activator, alanine type activator, lauryliminodipropionic acid; nonionic surfactants such as polyoxyethylene octyl ether, polyoxyethylene decyl ether, polyoxyethylene lauryl ether, polyoxyethylene lauryl amine, polyoxyethylene oleyl amine, polyoxyethylene polystyryl phenyl ether, polyoxyalkylene polystyryl phenyl ether, etc., nonionic surfactants of polyoxyalkylene parimary alkyl ether or polyoxyalkylene secondary alkyl ether, and nonionic surfactants of other polyoxyalkylenes such as polyoxyethylene dilaurate, polyoxyethylene laurate, polyoxyethylenated castor oil, polyoxyethylenated hardened castor oil, sorbitan lauric acid ester, polyoxyethylene sorbitan lauric acid ester, fatty acid diethanol amide; fatty acid alkyl esters such as octyl stearate and trimethylolpropane tridecanoate; and polyether polyols such as polyoxyalkylene butyl ether, polyoxyalkylene oleyl ether and trimethylolpropane tris (polyoxyalkylene) ether. Further, two or more of the above dispersants can be used as a mixture.

<Polyamide Acid>

In the present invention, polyamide acids obtained by polymerizing any tetracarboxylic acid dianhydride and diamine may be used without particular limitation. The amount of the tetracarboxylic acid dianhydride and the diamine used is not particularly limited, but is preferably 0.50 to 1.50 moles, more preferably 0.60 to 1.30 moles, 0.70 to 1.20 moles, per 1 mole of the tetracarboxylic dianhydride.

The tetracarboxylic acid dianhydride can be appropriately selected from tetracarboxylic acid dianhydrides that have hitherto been used as a material for synthesis of polyamide acids. The tetracarboxylic dianhydride may be an aromatic tetracarboxylic dianhydride or an aliphatic tetracarboxylic dianhydride. Preferably, however, from the viewpoint of heat resistance of the resultant polyimide resin, the use of aromatic tetracarboxylic acid dianhydride is preferred. Two or more tetracarboxylic acid dianhydrides may be used in combination.

Specific examples of preferred aromatic tetracarboxylic dianhydrides include pyromellitic dianhydride, 1,1-bis (2,3-dicarboxyphenyl) ethane dianhydride, bis (2,3-dicarboxyphenyl) methane dianhydride, bis (3,4-dicarboxyphenyl) methane dianhydride, 3,3',4,4'-biphenyltetracarboxylic dianhydride, 2,3,3',4'-biphenyltetracarboxylic dianhydride, 2,2,6,6-biphenyltetracarboxylic dianhydride, 2,2-bis(3,4-dicarboxyphenyl) propane dianhydride, 2,2-bis (2,3-dicarboxyphenyl) propane dianhydride, 2,2-bis(3,4-dicarboxyphenyl)-1,1,1,3,3,3-hexafluoropropane dianhydride, 2,2-bis (2,3-dicarboxyphenyl)-1,1,1,3,3,3-hexafluoropropane dianhydride, 3,3',4,4'-benzophenonetetracarboxylic dianhydride, bis(3,4-dicarboxyphenyl) ether dianhydride, bis(2,3-dicarboxyphenyl) ether dianhydride, 2,2',3,3'-benzophenonetetracarboxylic dianhydride, 4,4-(p-phenylenedioxy) diphthal acid dianhydride, 4,4-(m-phenylenedioxy) diphthalic acid dianhydride, 1,2,5,6-naphthalenetetracarboxylic dianhydride, 1,4,5,8-naphthalenetetracarboxylic acid dianhydride, 2,3,6,7-naphthalenetetracarboxylic dianhydride, 1,2,3,4-benzenetetracarboxylic dianhydride, 3,4,9,10-perylenetetracarboxylic dianhydride, 2,3,6,7-anthracenetetracarboxylic dianhydride, 1,2,7,8-phenanthrene tetracarboxylic dianhydride, fluorene 9,9-bis phthalic anhydride, 3,3',4,4'-diphenylsulfone tetracarboxylic acid dianhydride, and the like. Examples of aliphatic tetracarboxylic dianhydrides include ethylene tetracarboxylic dianhydride, butanetetracarboxylic dianhydride, cyclopentane tetracarboxylic dianhydride, cyclohexane tetracarboxylic dianhydride, 1,2,4,5-cyclohexane tetracarboxylic dianhydride, 1,2,3,4-cyclohexane tetracarboxylic dianhydride, and the like. Among them, 3,3',4,4'-biphenyltetracarboxylic acid dianhydride and pyromellitic acid dianhydride are preferred from the viewpoints of, for example, price and easy availability. These tetracarboxylic dianhydrides can be used alone or in combination of two or more.

The diamine can be appropriately selected from diamines that have hitherto been used as materials for synthesis of polyamide acids. This diamine may be either an aromatic diamine or an aliphatic diamine. Preferably, however, from the viewpoint of the heat resistance of the resultant polyimide resin, an aromatic diamine is preferable. Two or more of these diamines may be used in combination.

Aromatic diamines include diamino compounds in which one phenyl group or about 2 to 10 phenyl groups are bonded. Specific examples thereof include phenylenediamine and derivatives thereof, diaminobiphenyl compounds and derivatives thereof, diaminodiphenyl compounds and derivatives thereof, diaminotriphenyl compounds and derivatives thereof, diaminonaphthalene and derivatives thereof, aminophenylaminoindane and derivatives thereof, diaminotetraphenyl compounds and derivatives thereof, diaminohexaphenyl compounds and derivatives thereof, and cardo-type fluorenediamine derivatives.

Examples of phenylenediamines include m-phenylenediamine and p-phenylenediamine. Examples of phenylenediamine derivatives include diamines to which alkyl groups such as methyl group and ethyl group are bonded, for example, 2,4-diaminotoluene and 2,4-triphenylene diamine.

Diaminobiphenyl compounds are those including two aminophenyl groups bonded to each other through phenyl groups. Examples thereof include 4,4'-diaminobiphenyl, 4,4'-diamino-2,2'-bis (trifluoromethyl) biphenyl and the like.

The diaminodiphenyl compounds are those including two aminophenyl groups bonded to each other via another group. The bond is an ether bond, a sulfonyl bond, a thioether bond, a bond by an alkylene or a derivative group thereof, an imino bond, an azo bond, a phosphine oxide bond, an amide bond, an ureylene bond or the like. In the alkylene bond, the number of carbon atoms is about 1 to 6 and its derivative group is one in which one or more hydrogen atoms of an alkylene group is substituted with a halogen atom or the like.

Examples of diaminodiphenyl compounds include 3,3'-diaminodiphenyl ether, 3,4'-diaminodiphenyl ether, 4,4'-diaminodiphenyl ether, 3,3'-diaminodiphenyl sulfone, 3,4'-diaminodiphenyl sulfone, 4,4'-diaminodiphenyl sulfone, 3,3'-diaminodiphenylmethane, 3,4'-diaminodiphenylmethane, 4,4'-diaminodiphenylmethane, 4,4'-diaminodiphenyl sulfide, 3,3'-diaminodiphenyl ketone, 3,4'-diaminodiphenyl ketone, 2,2-bis(p-aminophenyl)propane, 2,2'-bis(p-aminophenyl)hexafluoropropane, 4-methyl-2,4-bis(p-aminophenyl)-1-pentene, 4-methyl-2,4-bis(p-aminophenyl)-2-pentene, iminodianilin, 4-methyl-2,4-bis(p-aminophenyl) pentane, bis(p-aminophenyl) phosphine oxide, 4,4'-diaminoazobenzene, 4,4'-diaminodiphenylurea, 4,4'-diaminodiphenylamide, 1,4-bis (4-aminophenoxy)benzene, 1,3-bis (4-aminophenoxy)benzene, 1,3-bis(3-aminophenoxy)benzene, 4,4'-bis(4-aminophenoxy)biphenyl, bis[4-(4-aminophenoxy) phenyl] sulfone, bis[4-(3-aminophenoxy) phenyl] sulfone, 2,2-bis[4-(4-aminophenoxy)phenyl] propane, 2,2-bis[4-(4-aminophenoxy)phenyl] hexafluoropropane and the like.

Among them, p-phenylenediamine, m-phenylenediamine, 2,4-diaminotoluene, and 4,4'-diaminodiphenyl ether are preferable, for example, from the viewpoint of price and easy availability.

The diaminotriphenyl compound is one in which two aminophenyl groups and one phenylene group are bonded via another group, and the other groups are selected from those similar to the diaminodiphenyl compound. Examples of diaminotriphenyl compounds can include 1,3-bis(m-aminophenoxy)benzene, 1,3-bis(p-aminophenoxy)benzene and 1,4-bis(p-aminophenoxy)benzene.

Examples of diaminonaphthalenes can include 1,5-diaminonaphthalene and 2,6-diaminonaphthalene.

Examples of aminophenylaminoindanes can include 5 or 6-amino-1-(p-aminophenyl)-1,3,3-trimethylindane.

Examples of diaminotetraphenyl compounds can include 4,4'-bis(p-aminophenoxy)biphenyl, 2,2'-bis[p-(p'-aminophenoxy)phenyl] propane, 2,2'-bis[p-(p'-aminophenoxy)biphenyl]propane, 2,2'-bis [p-(m-aminophenoxy)phenyl]benzophenone and the like.

Examples of cardo-type fluorene diamine derivatives can include 9,9-bisaniline fluorene and the like.

Examples of aliphatic diamines include those having about 2 to 15 carbon atoms, and specific examples thereof include pentamethylene diamine, hexamethylene diamine, heptamethylene diamine, and the like.

Not here that the diamine may be a compound in which the hydrogen atom is substituted with at least one substituent selected from the group consisting of a halogen atom, a methyl group, a methoxy group, a cyano group, a phenyl group, and the like.

Polyamide acids used in the present invention may be produced by any methods without particular limitation, and examples thereof include a well-known method in which an acid and a diamine component are reacted in an organic solvent.

The reaction between the tetracarboxylic acid dianhydride and the diamine is usually carried out in an organic solvent.

The organic solvent used for the reaction between the tetracarboxylic acid dianhydride and the diamine is not particularly limited as long as it can dissolve the tetracarboxylic acid dianhydride and the diamine, and does not react with the tetracarboxylic acid dianhydride and the diamine. Organic solvents can be used alone or as a mixture of two or more.

Examples of organic solvents used in the reaction of tetracarboxylic dianhydride and diamine include nitrogen-containing polar solvents such as N-methyl-2-pyrrolidone, N,N-dimethylacetamide, N,N-diethylacetamide, N,N-dimethyl formamide, N,N-diethylformamide, N-methyl caprolactam, N,N,N',N'-tetramethylurea; lactone-based polar solvents such as β-propiolactone, γ-butyrolactone, γ-valerolactone, δ-valerolactone, γ-caprolactone, and ε-caprolactone; dimethyl sulfoxide; acetonitrile; fatty acid esters such as ethyl lactate and butyl lactate; ethers such as diethylene glycol dimethyl ether, diethylene glycol diethyl ether, dioxane, tetrahydrofuran, methyl cellosolve acetate, ethyl cellosolve acetate; and phenolic solvents such as cresols. These organic solvents may be used alone or in a combination of two or more. Among them, a combination of the nitrogen-containing polar solvent and the lactone-based polar solvent is preferred. The amount of the organic solvent used is not particularly limited, but desirably it is the content such that the content of the polyamide acid generated is preferably 5 to 50% by mass.

Among these organic solvents, because of the solubility of polyamide acid to be generated, nitrogen-containing polar solvents such as N-methyl-2-pyrrolidone, N,N-dimethylacetamide, N,N-diethylacetamide, N,N-dimethylformamide, N,N-diethylformamide, N-methylcaprolactam, and N,N,N',N'-tetramethylurea are preferred. From the viewpoint of film formation and the like, a mixed solvent containing a lactone-based polar solvent such as γ-butyrolactone added thereto may be used, and the content of the lactone-based polar solvent in the whole organic solvent is 1 to 20% by mass, more preferably 5 to 15% by mass.

The polymerization temperature is generally −10 to 120° C., preferably 5 to 30° C. The polymerization time varies depending on the material composition used, but is usually 3 to 24 hours. Further, the intrinsic viscosity of the polyamide acid solution obtained under such conditions is preferably in the range of 1000 to 100000 cPs (centipoises), and more preferably in the range of 5000 to 70000 cPs.

<Polyimide>

In the polyimide used in the present invention, the structure and the molecular weight are not particularly limited, and well-known polyimides are usable as long as the polyimides are soluble in organic solvents used for varnish of the present invention. The polyimide may have on its side chain a condensable functional group such as a carboxy group or a functional group that promotes a crosslinking reaction or the like during burning.

In order to render the polyimide soluble in organic solvents, the use of monomers for introducing a flexible bend structure in the main chain, for example, aliphatic diamines such as ethylenediamine, hexamethylenediamine, 1,4-diaminocyclohexane, 1,3-diaminocyclohexane, 4,4'-diaminodicyclohexylmethane; aromatic diamines such as 2-methyl-1,4-phenylenediamine, o-tolidine, m-tolidine, 3,3'-dimethoxybenzidine, and 4,4'-diaminobenzanilide; polyoxyalkylene diamines such as polyoxyethylene diamine, polyoxypropylene diamine, and polyoxybutylene diamine; polysiloxane diamine; and acid anhydrides such as 2,3,3',4'-oxydiphthalic anhydride, 3,4,3',4'-oxydiphthalic anhydride, 2,2-bis(4-hydroxyphenyl)propane dibenzoate-3, 3',4,4'-tetracarboxylic dianhydride is effective. Further, the use of monomers having a functional group that improves solubility in organic solvents, for example, fluorinated diamines such as 2,2'-bis(trifluoromethyl)-4,4'-diaminobiphenyl, 2-trifluoromethyl-1,4-phenylenediamine is also effective. Furthermore, in addition to the monomers for improving the solubility of the polyimide, the same monomers as described above in connection with the polyamide acids can also be used in combination as long as the solubility is not impaired.

The polyimide soluble in organic solvents used in the present invention may be produced by any well-known methods without particular limitation, for example, a method in which a polyamide acid is chemically imidized or heat-imidized followed by dissolution in an organic solvent. Examples of such polyimides can include aliphatic polyimides (wholly aliphatic polyimides), aromatic polyimides, and the like, and aromatic polyimides are preferred. Aromatic polyimides include those produced by subjecting a polyamide acid containing a repeating unit represented by the formula (1) to heat or chemical ring-closing reaction, or by dissolving a polyimide having a repeating unit represented by the formula (2) in a solvent. In the formula, Ar represents an aryl group.

[Chem. 9]

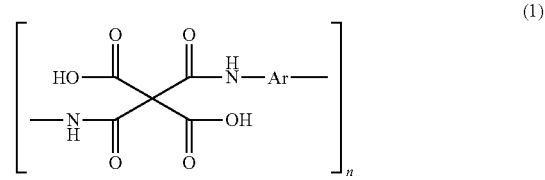

(1)

[Chem. 10]

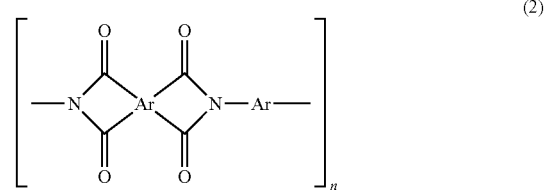

(2)

<Polyamideimide>

For the polyamideimide used in the present invention, the structure and the molecular weight are not particularly limited, and well-known polyamideimides can be used as long as the polyamideimides are soluble in organic solvents used for varnish in the present invention. The polyamideimide may have on its side chain a condensable functional group such as a carboxy group or a functional group that promotes a crosslinking reaction or the like during burning.

Further, polyamideimides produced by reacting any trimellitic anhydride with diisocyanate, or by reacting any reactive derivative of trimellitic anhydride with a diamine to give a precursor polymer and imidizing the precursor polymer may be used without particular limitation.

Examples of any trimellitic anhydrides or reactive derivatives thereof mentioned above include trimellitic anhydrides, trimellitic anhydride acid halides such as trimellitic anhydride chloride, and trimellitic anhydride esters.

Examples of any diisocyanates include meta-phenylene diisocyanate, p-phenylene diisocyanate, o tolidine diisocyanate, p-phenylene diisocyanate, m-phenylene diisocyanate, 4,4'-oxybis (phenyl isocyanate), 4,4'-diisocyanate diphenyl-methane, bis[4-(4-isocyanate phenoxy)phenyl]sulfone, 2,2'-bis[4-(4-isocyanate phenoxy)phenyl]propane, 2,4-tolylene diisocyanate, 2,6-tolylene diisocyanate, 4,4'-diphenylmethane diisocyanate, 3,3'-dimethylphenyl-4,4'-diisocyanate, 3,3'-diethylphenyl-4,4'-diisocyanate, isophorone diisocyanate, hexamethylene diisocyanate, 4,4'-dicyclohexylmethane diisocyanate, m-xylene diisocyanate, p-xylene diisocyanate, naphthalene diisocyanate and the like.

Any diamines mentioned above include those exemplified above in connection with the polyamide acid.

<Organic Solvent>

The organic solvent used for the varnish is not particularly limited as long as it can dissolve the polyamide acid and/or the polyimide-based resin and does not dissolve the fine particles. Examples thereof include those exemplified above in connection with solvents used in the reaction between the tetracarboxylic dianhydride and the diamine. The solvent may be used singly and two or more thereof may be used in combination.

Among all components in the varnish, the content of the mixed solvent (S) is preferably from 50 to 95% by mass, and more preferably from 60 to 85% by mass. The solid content of the varnish is preferably 5 to 50% by mass, and more preferably 15 to 40% by mass.

Further, in the manufacturing method to be described later, when the unburned composite membrane is formed as a two-layered unburned composite membrane, the volume ratio of the polyamide acid, polyimide or polyamideimide (A1) and fine particles (B1) in the first varnish is preferably 19:81 to 45:65. When the fine particle volume is 65 or more when the total volume is presumed to be 100, the particles are uniformly dispersed, and when the fine particle volume is 81 or less, the particles do not agglomerate and are dispersed, so that pores are uniformly formed on the substrate side of the polyimide-based resin molded membrane. In the second varnish, the volume ratio of the polyamide acid, polyimide or polyamideimide (A2) to the fine particles (B2) is preferably 20:80 to 50:50. When the fine particle volume is 50 or more when the total volume is presumed to be 100, the particles are uniformly dispersed, and when the fine particle volume is 80 or less, the particles do not agglomerate, and cracks and the like do not occur on the surface. Accordingly, polyimide-based resin porous membranes having favorable mechanical properties such as stress resistance and fracture elongation can be stably formed.

Regarding the volume ratio, the second varnish preferably has a smaller particle content ratio than the first varnish. When the above requirement is satisfied, even in filling of fine particles in the polyamide acid, polyimide, or polyamideimide at a high density, the strength and flexibility of the unburned composite membrane, the polyimide-based resin-fine particle composite membrane, and the polyimide-based resin porous membrane can be ensured. Further, the production cost can be lowered by providing a layer having a low fine particle content.

In addition to the above components, for the purposes of antistatic properties, imparting flame retardancy, performing low-temperature burning, releasability, coatability, etc., well-known additives, for example, antistatic agents, flame retardants, chemical imidizing agents, condensing agents, release agents, and surface modifiers can be incorporated according to need.

[Production of Unburned Composite Membrane]

Regarding the molding of the unburned composite membrane containing the polyamide acid or the polyimide-based resin and the fine particles, film formation is carried out by coating a substrate with the varnish and drying the coating at 0 to 120° C. (preferably 0 to 100° C.) under atmospheric pressure or in vacuum, more preferably at 60 to 95° C. (still more preferably at 65 to 90° C.) under atmospheric pressure. The coating thickness is, for example, 1 to 500 μm, preferably 5 to 200 μm, and more preferably 5 to 50 μm. Note here that a release layer may be provided on the substrate, if necessary. Further, in the production of the unburned composite membrane, before the production (burning step) of the polyimide-based resin-fine particle composite membrane to be described later, the step of dipping in a solvent containing water, the step of pressing, the step of drying after the dipping step may be optionally provided.

The release layer may be prepared by coating a release agent on a substrate and drying or baking the coating. Well-known release agents such as alkyl phosphate ammonium salt-based and fluorine-based or silicone release agents can be used as the release agent without particular limitation. When the unburned composite membrane containing the dried polyamide acid or polyimide-based resin and fine particles is released from the substrate, the release agent remains slightly on the release surface of the unburned composite membrane. Since the remaining release agent can affect the wettability of the surface of the porous polyimide-based resin membrane and contamination of impurities, the remaining release agent is preferably removed.

Therefore, preferably, the unburned composite membrane separated from the substrate is cleaned with organic solvents or the like. The unburned composite membrane may be cleaned by a method selected from well-known methods such as a method in which the unburned composite membrane is dipped in a cleaning solution and is then taken out, and a method in which shower cleaning is carried out. Furthermore, in order to dry the unburned composite membrane after cleaning, well-known methods such as air-drying of the unburned composite membrane after cleaning at room temperature, warming to an appropriate predetermined temperature in a thermostatic chamber, etc. may be applied without particular limitation. For example, a method in which the end of the unburned composite membrane is fixed to SUS frame or the like can also be employed to prevent deformation.

On the other hand, when a substrate is used as it is without providing a release layer in film formation of the unburned composite membrane, the step of forming the release layer and the step of cleaning the unburned composite membrane can be omitted.

When the unburned composite membrane is formed in a two-layered structure, a substrate such as a glass substrate is coated with the first varnish as it is and drying the coating at 0 to 120° C. (preferably 0 to 90° C.) under atmospheric pressure or in vacuum, more preferably at 10 to 100° C. (still more preferably 10 to 90° C.) under atmospheric pressure to form a first unburned composite membrane having a thickness of 1 to 40 μm.

Subsequently, the formed first unburned composite membrane is coated with the second varnish, and, in the same manner as the first unburned composite membrane, the coating is dried at 0 to 80° C. (preferably 0 to 50° C.) more preferably at 10 to 80° C. (still more preferably 10 to 30° C.) under atmospheric pressure to form a second unburned composite membrane having a layer thickness of 5 to 150 μm. Thus, a two-layered unburned composite membrane is obtained.

[Production of Polyimide-Based Resin-Fine Particle Composite Membrane (Burning Step)]

The dried unburned composite membrane (or the two-layered unburned composite membrane; the same shall apply hereinafter) is subjected to heat post treatment (burning) to form a composite membrane composed of a polyimide-based resin and fine particles (a polyimide-based resin-fine particle composite membrane). When the varnish contains a polyamide acid, preferably, imidization is completed at the step of burning. Note here that the burning step is an optional step. In particular, when polyimide or polyamideimide is used as a varnish, the burning step may be omitted.

The burning temperature varies depending on the structure of the polyamide acid or polyimide-based resin contained in the unburned composite membrane or the presence or absence of a condensing agent, but is preferably from 120 to 400° C., and more preferably from 150 to 375° C.

In burning, the burning step is not necessarily separated from the drying step. For example, when burning is carried out at 375° C., methods usable herein include a method including raising the temperature from room temperature to 375° C. over a period of 3 hours, keeping the material at 375° C. for 20 minutes, or a stepwise drying-thermal imidization method including raising the temperature stepwise from room temperature to 375° C. (keeping each step for 20 minutes) and finally keeping it at 375° C. for 20 minutes. At that time, a method of fixing the end of the unburned composite membrane to SUS frame or the like may also be employed to prevent deformation.

The thickness of the finished polyimide-based resin-fine particle composite membrane, in the case where it is a film, for example, can be determined by measuring and averaging the thicknesses of a plurality of portions using a micrometer or the like. A preferred average thickness varies depending upon the use of the polyimide-based resin-fine particle composite membrane or the polyimide-based resin porous membrane. For example, when the product is used in separating materials, adsorbing materials or the like, a small thickness is preferred. For example, the thickness may be 1 µm or more, preferably 5 to 500 µm, and more preferably 8 to 100 µm.

[Particulate Removing Step (Porous Formation of Polyimide-Based Resin-Fine Particle Composite Membrane)]

The polyimide-based resin porous membranes having micropores can be produced with favorable reproducibility by removing the fine particles from the polyimide-based resin-fine particle composite membrane by an appropriately selected method. For example, when silica is used as the fine particles, the polyimide-based resin-fine particle composite membrane can be made porous by dissolving and removing silica with low-concentration hydrogen fluoride water (HF) or the like. Furthermore, when the fine particles are resin fine particles, the resin fine particles can be removed by heating the material to a temperature equal to or above the thermal decomposition temperature of the resin fine particles as described above and below the thermal decomposition temperature of the polyimide-based resin to decompose the resin fine particles.

[Imide Bond Ring-Opening Step]

The method for producing a polyimide-based resin porous membrane of the present invention includes an imide bond ring-opening step as described above. Specifically, this step may be carried out by (a) a method in which, before the fine particle removing step, the polyimide-based resin-fine particle composite membrane is subjected to the imide bond ring-opening step, or alternatively, (b) a method in which, after the fine particle removing step, the polyimide-based resin molded membrane that has been rendered porous by the step is subjected to the imide bond ring-opening step. In the method for producing (a), the imide bond that exists on the outer surface and near the outer surface of the polyimide-based resin molded membrane can be ring-opened and the object of the present invention can be attained. The latter method (b), however, is preferred because the porosity of the resultant polyimide-based resin porous membrane can be enhanced.

The imide bond ring-opening step can be carried out by a chemical etching method, a physical removal method, or a combination thereof. The chemical etching method is not particularly limited, and for example, a well-known method can be used.

Treatment with a chemical etching solution such as an inorganic alkaline solution or an organic alkaline solution can be mentioned as the chemical etching method. Inorganic alkaline solutions are preferred. Examples of inorganic alkaline solutions include a hydrazine solution containing hydrazine hydrate and ethylenediamine, a solution of an alkali metal hydroxide such as potassium hydroxide, sodium hydroxide, sodium carbonate, sodium silicate, sodium metasilicate, etc., an ammonia solution, and an etching solution composed of an alkali hydroxide, hydrazine and 1,3-dimethyl-2-imidazolidinone as main components. Examples of organic alkaline solutions include primary amines such as ethylamine and n-propylamine; secondary amines such as diethylamine and di-n-butylamine; tertiary amines such as triethylamine and methyldiethylamine; alcohol amines such as dimethyl ethanol amine and triethanolamine; quaternary ammonium salts such as tetramethylammonium hydroxide and tetraethylammonium hydroxide; and cyclic amines such as pyrrole and piperidine.

For solvents of each of the solutions, pure water and alcohols can be appropriately selected. It is also possible to use those in which an appropriate amount of surfactant has been added. The alkali concentration is, for example, 0.01 to 20% by mass.

Further, physical methods include, for example, plasma etching (oxygen, argon, etc.), dry etching by corona discharge, or the like.

The above methods are preferred because they can be applied to any imide bond ring-opening step before the fine particle removing step or after the fine particle removing step. When the chemical etching method is carried out after the fine particle removing step, communicating pores can easily be formed within the polyimide-based resin porous membrane, contributing to improved porosity.

When the chemical etching method is used as the imide bond ring-opening step, a cleaning step of the polyimide-based resin porous membrane may be carried out again to remove excessive etching solution components. Cleaning after chemical etching may be performed by cleaning with water alone, but a combination of acid cleaning and/or water cleaning is preferable. The polyimide-based resin porous membrane may be again subjected to the burning step to improve the wettability of the surface of the polyimide-based resin porous membrane to the organic solvent and to remove the remaining organic substances. As with burning conditions in [manufacture of polyimide-based resin-fine particle composite membrane (burning step)], burning conditions may be properly determined.

[Specific Purification Method Using the Above-Mentioned Liquid or Silicon Compound-Containing Liquid as Object to be Purified]

The purification method for purifying a liquid or a silicon compound-containing liquid as an object to be purified according to the first aspect and the second aspect, includes allowing some or all of the liquid to permeate through from one side to the other side of the above-mentioned polyimide and/or polyamideimide porous membrane by way of a differential pressure.

In the purification method for purifying a liquid or a silicon compound-containing liquid as an object to be purified according to the first and second aspects, some or all of the liquid can be ordinarily allowed to permeate from one side to the other side of the polyimide porous membrane described above by filtering the part or all of the liquid through the polyimide-based resin porous membrane as a separating material or an adsorbing material. The polyimide-based resin porous membrane used as the separating material or the adsorbing material may be incorporated in a filter device to be described later.

In the purification method for purifying a liquid or a silicon compound-containing liquid as an object to be purified according to the first and second aspects, the polyimide-based resin porous membrane may be used in a flat form or in the form of a pipe formed by combining opposite sides of the polyimide-based resin porous membrane. Preferably, the pipe-shaped polyimide-based porous membrane is in a folded form from the viewpoint of increasing the area of contact with the feed liquid. As mentioned later, the polyimide-based resin porous membrane is properly subjected to sealing treatment so that the feed liquid is mixed with the filtrate.

The purification of the a liquid or a silicon compound-containing liquid may also be carried out using the polyimide-based porous membrane described above without applying a differential pressure, that is, by gravitational natural filtration, but is preferably carried out by taking advantage of a differential pressure. The differential pressure is not particularly limited as long as a pressure difference is provided between one side and the other side of the polyimide-based resin porous membrane. In general, however, for example, pressurizing (positive pressure) in which pressure is applied to one side (feed liquid side) of the polyimide-based resin porous membrane, depressurizing (negative pressure) in which one side (filtrate side) of the polyimide-based resin porous membrane is brought to a negative pressure may be mentioned, and the pressurizing is preferred.

Pressure is applied to the side of the polyimide-based resin porous membrane (feed liquid side) in which a liquid or a silicon compound-containing liquid (which may be referred to as "feed liquid" in this specification) before allowing to permeate through the polyimide-based resin porous membrane exists. It is preferable to apply pressure by utilizing, for example, the hydraulic pressure generated by circulating or feeding of the feed liquid or using the positive pressure of gas. The hydraulic pressure can be generated, for example, by a positive hydraulic pressure adding method such as a pump (liquid feeding pump, circulating pump, etc.), and specifically, a rotary pump, a diaphragm pump, a metering pump, a chemical pump, a plunger pump, a bellows pump, a gear pump, a vacuum pump, an air pump, a liquid pump, and the like. The hydraulic pressure may be, for example, the pressure applied to the polyimide-based resin porous membrane by the a liquid or a silicon compound-containing liquid when allowing the a liquid or a silicon compound-containing liquid to permeate through the polyimide-based resin porous membrane according to only gravity, but it is preferable that pressure is applied by the positive hydraulic pressure application method. As the gas used for pressurization, a gas which is inert or nonreactive with respect to the feed liquid is preferable, and specific examples thereof include nitrogen, a rare gas such as helium, argon, and the like. In the field of manufacturing electronic materials, particularly semiconductors and the like, pressurization is preferable. In that case, the side to collect the liquid or silicon compound-containing liquid permeating through the polyimide-based resin porous membrane may be atmospheric pressure that does not decompress, and as for pressurization, positive pressure of gas is preferred. In the pressurizing method, a valve such as a pressurizing valve, a pressurizing valve or a three-way valve may be used. The reduced pressure is for depressurizing the side (filtrate side) where the liquid or silicon compound-containing liquid permeating through the polyimide-based resin porous membrane is collected. For example, it may be depressurizing by a pump, but it is preferable to depressurize to vacuum. In the case of circulating or feeding a feed solution by a pump, usually the pump is disposed between a feed liquid tank (or circulation tank) and a polyimide-based resin porous membrane.

The pressurization may use both the hydraulic pressure and the positive pressure of gas. Further, the differential pressure may be a combination of pressurization and depressurization, for example, it may be use of both of hydraulic pressure and depressurizing, use of both of positive pressure and depressurizing of gas, and use of hydraulic pressure and positive pressure and depressurizing of gas. When a method of providing a differential pressure is combined, a combination of a hydraulic pressure and a positive pressure of gas, and a combination of a hydraulic pressure and depressurizing are preferable from the viewpoint of ease of manufacturing and the like. In the present invention, since the polyimide-based resin porous membrane is used, as a method of providing a differential pressure, for example, purification excellent in impurity removal capability can be performed even by one method such as positive pressure of gas.

By providing the differential pressure, the pressure difference applied to the front and back of the polyimide-based resin porous membrane may be set appropriately depending on the thickness, the porosity or the average pore diameter of the polyimide-based resin porous membrane to be used, or the desired purifying degree, the flow amount, the flow rate, the concentration or viscosity of the feed liquid or the like. For example, in the case of the so-called cross flow method (the feed liquid is allowed to flow in parallel to the polyimide-based resin porous membrane), it is, for example, 3 MPa or less. In the case of a so-called dead end system (flowing the feed liquid so as to intersect the polyimide-based resin porous membrane), it is, for example, 1 MPa or less. The lower limit value is not particularly limited, and is, for example, 10 Pa.

In the purification method for purifying a liquid or a silicon compound-containing liquid as an object to be purified according to the first and second aspects, when some or all of the liquid or silicon compound-containing liquid is allowed to permeate from one side to the other side of the polyimide-based resin porous membrane, when the liquid or silicon compound-containing liquid contains a solute, the feed solution may be appropriately diluted.

In the purification method for purifying a liquid or a silicon compound-containing liquid as an object to be purified according to the first and second aspects, before the feed liquid is allowed to permeate, a solution of an alcohol such as methanol, ethanol, isopropyl alcohol or the like or a ketone such as acetone, methyl ethyl ketone or the like, water, a solvent contained in the feed liquid, or a mixture thereof may be brought into contact with the polyimide-based resin porous membrane and allowed to pass therethrough so that the polyimide-based resin porous membrane is cleaned or is improved in wettability with respect to the feed liquid or for adjusting the surface energy of the polyimide-based resin porous membrane and the feed liquid. In the contact between the solution before permeating through the feed liquid and the polyimide-based resin porous membrane, the polyimide-based resin porous membrane may be impregnated with or immersed in the solution. And the polyimide-based resin porous membrane may be brought into contact with the solution to allow the solution to infiltrate also into, for example, the pores inside the polyimide-based resin porous membrane. The contact between the solution before permeating through the feed liquid and the polyimide-based resin porous membrane may be carried out by the differential pressure as mentioned above, and may also be carried out under pressure, particularly in the case of penetrating the solution into the pores inside the polyimide-based resin porous membrane.

Since the polyimide-based resin porous membrane of the present invention is a porous membrane including polyimide and/or polyamideimide as a main component which may contain at least one selected from the group consisting of a carboxy group, a salt type carboxy group and an —NH— bond, and is a porous membrane having a high degree of porosity as described above, it can be suitably used as a separating material and an adsorbing material. The polyimide-based resin porous membrane of the present invention is a porous membrane having communicating pores, and is preferably a porous membrane having communicating pores in which a pore having a curved inner surface is formed as described above, more preferably, since it is a porous membrane having communicating pores having a structure in which substantially spherical pores are in communication with each other, when a liquid is allowed to permeate through the porous membrane, impurities including elements being solid at ordinary temperature and is contained in the liquid or silicon compound-containing liquid can be partially or entirely removed from the liquid or silicon compound-containing liquid.

In the present specification, "elements being solid at ordinary temperature" means elements constituting a simple substance which is solid at ordinary temperature, for example, at room temperature, specifically 20° C. For example, when the element is Fe, since iron as a simple substance of Fe element is solid at ordinary temperature, it corresponds to "elements being solid at ordinary temperature" in the present invention. "Elements being solid at ordinary temperature" usually include metal elements, metalloid elements, and some nonmetallic elements. Examples of the metal element include alkali metals such as Li, Na and K; alkaline earth metals such as Be, Mg, Ca, Ba and the like; transition metals belonging to Groups 3 to 11, such as Cr, Mn, Fe, Co, Ni, Cu and Zn of the periodic table; metals belonging to Groups 12 to 15 of the periodic table, such as Zn, Al, Ga, and Sn. Examples of metalloid elements include B, Si, Ge, As, Sb, Te, Po, and the like. Some nonmetallic elements include C, P, S, I and the like. In the present invention, the "elements being solid at ordinary temperature" are preferably a metal element or a metalloid element, more preferably a metallic element, and still more preferably iron and/or zinc.

In the present specification, "impurities including elements being solid at ordinary temperature" means impurities containing the "elements being solid at ordinary temperature", and may be a simple substance of the element, or may be a compound including a plurality of elements having the element.

The purification method for purifying a liquid or a silicon compound-containing liquid as an object to be purified according to the first and second aspects is particularly preferably applied when the impurity is a metal impurity containing a metal element, in view of high need for removal from a silylating agent liquid or the like, for example, in the field of manufacturing electronic materials such as semiconductors. By using the polyimide-based resin porous membrane of the present invention, it is considered that a minute substance such as metal particles present in the liquid or silicon compound-containing liquid before treatment tends to adsorb to the pores and/or the communicating pores of the porous membrane. The polyimide-based resin porous membrane of the present invention may further have at least one selected from the group consisting of a carboxy group, a salt-type carboxy group and an —NH— bond. It is thought to be easy to absorb metal particles contained in the fluid, for example, metal ions or metal aggregates (for example, aggregates of metal oxides, aggregates of metals and organic substances) by the electric charge or Coulomb force provided in these groups, and to promote adsorption to the pores in the porous membrane and/or the porous membrane. Furthermore, it is considered that it can also function as an ion exchange membrane.

In the purification method for purifying a liquid or a silicon compound-containing liquid as an object to be purified according to the first and second aspects, since the polyimide-based resin porous membrane has a high degree of porosity and has communicating pores as described above, it is considered that some or all of the impurities including elements being solid at ordinary temperature can be removed from the liquid before treatment by separation and/or adsorption. In the present specification, "separation" may include at least one selected from the group consisting of filtration, isolation, removal, trapping, purification and sieving, and can also be used for wastewater treatment. The purification method for purifying a liquid or a silicon compound-containing liquid as an object to be purified according to the first and second aspects can also be suitably used for processing that will perform both separation and adsorption as a process for separating a minute substance from a liquid containing the minute substance by adsorbing a minute substance to pores and/or communicating pores and the like of the polyimide-based resin porous membrane.

As described above, the polyimide-based resin porous membrane of the present invention is a porous membrane containing pores preferably having an average pore diameter of several hundreds of nanometers. Thus, for example, even minute substances in the nanometer unit can be adsorbed or trapped in pores and/or communicating pores in the membrane. Therefore, the purification method for purifying a liquid or a silicon compound-containing liquid as an object to be purified according to the first and second aspects using the polyimide-based resin porous membrane can be applied in the field of electronic materials requiring extremely accurate impurity removal, particularly semiconductor manufacturing, and can be suitably applied in various purification methods for separating and/or adsorbing impurities from various liquids such as a silylating agent liquid or a silicon compound-containing liquid that is used for semiconductor manufacturing.

In the purification method for purifying a liquid or a silicon compound-containing liquid as an object to be purified according to the first and second aspects, the polyimide-based resin porous membrane can be used, for example, as a filter medium and other filtering materials. Specifically, it may be used alone or may be used as a filtering material with another functional layer (membrane) provided. Alternatively, it may be used as a membrane to be combined with another filter medium, for example, it can be used as a membrane for use in a filter device or the like. The functional layer that can be used in combination with the polyimide-based resin porous membrane of the present invention is not particularly limited, and examples thereof include nylon membranes, polytetrafluoroethylene (PTFE) membranes, tetrafluoroethylene/perfluoroalkylvinylether copolymer (PFA) membranes, membranes modified with them or the like having a chemical or physicochemical function.

In the purification method for purifying a liquid or a silicon compound-containing liquid as an object to be purified according to the first and second aspects, the polyimide-based resin porous membrane can be used for a filter medium such as a metal filter used in the field of, for example, semiconductor manufacturing, can also be used for a laminate including the filter medium and another filter material, and can also be used for a filter device. The filter device is not particularly limited, but in the filter device, the polyimide-based resin porous membrane is arranged so that the feed liquid and the filtrate cross each other. In relation to the liquid flow path, the porous membrane may be arranged in parallel to the flow path or may be arranged to intersect. Regions before and after allowing the liquid to pass through the polyimide-based resin porous membrane are appropriately sealed so that the feed liquid is separated from the filtrate. For example, as a method of sealing, the polyimide-based resin porous membrane of the present invention may be processed by adhesion by light (UV) curing or adhesion by heat (including adhesion due to an anchor effect (thermal welding or the like)) or by adhesion using an adhesive. Alternatively, the polyimide-based resin porous membrane of the present invention and another filter material (filter) can be adhesively bonded, for example, by an incorporation method or the like. The polyimide-based resin porous membrane may be further provided in an outer container made of a thermoplastic resin such as polyethylene, polypropylene, tetrafluoroethylene perfluoroalkylvinylether copolymer (PFA), polyethersulfone (PES), polyimide, polyamideimide or the like.

The filter medium of the fourth aspect described above is a filter medium which is composed of a polyimide and/or polyamideimide porous membrane used for the purification method for purifying a liquid or a silicon compound-containing liquid as an object to be purified according to the first and second aspects, and a filter device including a polyimide and/or polyamideimide porous membrane is also one of the present inventions.

The purification method for purifying a liquid or a silicon compound-containing liquid as an object to be purified according to the first and second aspects can be suitably used for removing metals contained in the above-mentioned silylating agent liquid and the like used in the field of semiconductor manufacturing. As metals, in particular, the removal rate of iron and zinc is high. The metal removal rate, to be described later, with respect to iron can be, for example, 90% or more, preferably 95% or more, more preferably 97% or more, and still more preferably 98% or more. The metal removal rate with respect to zinc can be, for example, 45% or more, preferably 50% or more, more preferably 60% or more. The metal removal rate with respect to zinc contained in pure water can be, for example, 80% or more, preferably 85% or more, more preferably 90% or more. In the case of using a polyimide-based resin porous membrane that has undergone an imide bond ring-opening step, it can also be, for example, 95% or more, and preferably 98% or more. The upper limit of the metal removal rate is preferably as high as possible, and it is not particularly set but for iron, for example, less than 100%, usually 99.5% or less when the liquid is an organic solvent and 99% or less when the liquid is pure water. For zinc, for example, it can be 100% or less, and in some cases it may be 99% or less.

Furthermore, when the purification method for purifying a liquid or a silicon compound-containing liquid as an object to be purified according to the first and second aspects is used for removing impurities such as metals contained in the above-mentioned silylating agent liquid and the like used in the field of semiconductor manufacturing, impurities can be removed with the flow rate of the fluid such as silylating agent liquid kept high. The flow rate in this case is not particularly limited, and the flow rate of pure water pressurized at 0.08 MPa at room temperature may be 1 ml/min or more, preferably 3 ml/min or more, more preferably 5 ml/min or more, and particularly preferably 10 ml/min or more. The upper limit is not particularly limited, and may be, for example, 50 ml/min. The purification method for purifying a liquid or a silicon compound-containing liquid as an object to be purified according to the first and second aspects is advantageous in that the impurity removal rate can be kept high while maintaining a high flow rate.

The purification method for purifying a liquid or a silicon compound-containing liquid as an object to be purified according to the first and second aspects uses a polyimide-based resin porous membrane containing polyimide and/or polyamideimide as a main component, so that it can maintain a high flow rate of a fluid such as a chemical solution, and it can be suitably applied to circulation type purification which allows the liquid such as chemical solutions to permeate through the polyimide-based resin porous membrane while constantly circulating the liquid. The polyimide-based resin porous membrane of the present invention is also excellent in mechanical properties such as stress and fracture elongation. For example, the stress can be, for example, preferably 10 MPa or more, more preferably 15 MPa or more, and still more preferably 15 to 50 MPa, and the fracture elongation can be, for example, 10% GL or more, and preferably 15% GL or more. The upper limit of the fracture elongation can be, for example, 50% GL, preferably 45% GL, and more preferably 40% GL. When the porosity is lowered, the fracture elongation tends to be increased.

[Method for Producing Silylating Agent Liquid, Film Forming Material, or Diffusing Agent Composition that is Used for Diffusing a Dopant into a Semiconductor Substrate]

A method for producing a silylating agent liquid, a film forming material, or a diffusing agent composition that is used for diffusing a dopant into a semiconductor substrate according to the third aspect uses the purification method for purifying a liquid or a silicon compound-containing liquid as an object to be purified according to the first and second aspects. Since the purification method for purifying a liquid or a silicon compound-containing liquid as an object to be purified according to the first and second aspects is excellent in purification effect as mentioned above, the method for producing according to the third aspect using such a purification method for purifying a liquid or a silicon compound-containing liquid as an object to be purified enables a silylating agent liquid, a film forming material, or a diffusing agent composition that is used for diffusing a dopant in a semiconductor substrate, in which the content of impurities is reduced, to be manufactured. In other words, the method for producing the silylating agent liquid, film forming material, or a diffusing agent composition that is used for diffusing a dopant in a semiconductor substrate according to the third aspect is a method for producing a silylating agent liquid, a film forming material or a diffusing agent composition. The method includes purifying a silylating agent liquid, a film forming material or a diffusing agent composition, as an object to be purified, by a purification method using a liquid or a silicon compound-containing liquid as an object to be purified according to the first and second aspects.

EXAMPLES

The present invention will be described more specifically with reference to Examples. However, the scope of the present invention is not limited to these Examples.

In the Examples and Comparative Examples, the following tetracarboxylic acid dianhydride, diamine, polyamide acid, polyamideimide, organic solvent, dispersant and fine particles were used. The particle size distribution index of silica (1) is about 3.3, and the particle size distribution index of silica (2) is about 1.5.

Tetracarboxylic dianhydride: pyromellitic dianhydride
Diamine: 4,4'-diaminodiphenyl ether
Polyamide acid solution: reaction product of pyromellitic acid dianhydride and 4,4'-diaminodiphenyl ether (solid content: 21.9% by mass (organic solvent: N,N-dimethylacetamide))
Organic solvent (1): N, N-dimethylacetamide (DMAc)
Organic solvent (2): Gamma butyrolactone
Dispersant: polyoxyethylene secondary alkyl ether-based dispersant
Fine particles:
Silica (1): silica having an average particle diameter of 700 nm
Silica (2): silica having an average particle diameter of 300 nm
Etching solution (1): A 1.1% by mass solution of NaOH in a mixed solution composed of methanol:water (mass ratio 3:7)

<Examples 1 to 4> Polyimide Porous Membrane

[Preparation of Silica Dispersion Liquid]
To a mixture of 23.1 parts by mass of the organic solvent (1) and 0.1 parts by mass of dispersant, 23.1 parts by mass of silica (1) or silica (2) having an average particle diameter specified in Table 1 was added, and the mixture was stirred to prepare a silica dispersion liquid.
[Preparation of Varnish]
42.0 parts by mass of the silica dispersion liquid obtained in Preparation of the silica dispersion liquid was added to 41.1 parts by mass of the polyamide acid solution. Further, the organic solvents (1) and (2) were respectively added so that the solvent composition in the entire varnish was organic solvent (1):organic solvent (2)=90:10, and the mixture was stirred to prepare a varnish. Note here that in the obtained varnish, the volume ratio of the polyamide acid to silica is 40:60 (mass ratio is 30:70).
[Film Formation of Unburned Composite Membrane]
The above varnish was applied on a polyethylene terephthalate (PET) film as a base material using an applicator to form a film. The film was prebaked at 90° C. for 5 minutes to produce an unburned composite membrane having a film thickness of 40 µm. After the unburned composite membrane was dipped in water for 3 minutes, it was pressed by allowing it to pass through between two rolls. At that time, the roll pressing pressure was 3.0 kg/cm$^2$, the roll temperature was 80° C., and the moving speed of the unburned composite membrane was 0.5 m/min. The unburned composite membrane was released from the base material to obtain an unburned composite membrane.
[Imidization of Unburned Composite Membrane]
The unburned composite membrane was heat-treated (burned) for 15 minutes at a temperature specified in Table 1 for imidization to obtain a polyimide-fine particle composite membrane.
[Formation of Polyimide Porous Membrane]
The polyimide-fine particle composite membrane obtained above was dipped in a 10% HF solution for 10 minutes to remove fine particles contained in the membrane, followed by washing with water and drying to obtain a polyimide porous membrane.
[Chemical Etching]
In Examples 1 and 2, as an imide bond ring-opening process, a polyimide porous membrane was dipped in a chemical etching solution (1) for 2 minutes and subjected to imide bond ring-opening process to obtain a polyimide porous membrane. Thereafter, re-burning was carried out at 340° C. for 15 minutes. In Examples 3 and 4, chemical etching as an imide bond ring-opening step and subsequent re-burning were not carried out.

<Comparative Example 1> Porous Membrane of Other Resin

A porous membrane made of polyamide (nylon) (pore size: about 10 nm or less, film thickness about 75 µm) as Comparative Example 1 was prepared.
<Evaluation>
For the porous membranes prepared above, the following evaluation was carried out respectively. The results are shown in Table 1.
[Metal Removal Rate]
Each prepared porous membrane was cut into a circle having a diameter of 47 mm and used as a filter material. After housing setting, 200 mL of isopropyl alcohol and 200 mL of butyl acetate were sequentially allowed to pass therethrough. Thereafter, the metal impurity-containing liquid prepared by adding iron into 0.2% by mass solution of tetraisocyanate silane in butyl acetate was measured for the content (A) of iron in the liquid containing metal impurities, and then was allowed to pass through the membrane while flowing under nitrogen pressure at 0.08 MPa. The content (B) of iron in the liquid after passing was measured, and the value expressed by the following formula was defined as the metal removal rate (%), and evaluation was carried out according to the following criteria.

$$(A-B)/B \times 100$$

However, since the membrane was broken at 0.08 MPa, the metal removal rate could not be calculated in the porous membrane made of polyethylene.

TABLE 1

| | Resin | Particles (Average particle diameter/nm) | Film thickness | Burning (15 minutes) | CE | Metal removal rate Fe (%) |
|---|---|---|---|---|---|---|
| Example 1 | Polyimide | 700 | 40 μm | 340° C. | Carried out | 95% or more |
| Example 2 | | 300 | 40 μm | 340° C. | Carried out | 95% or more |
| Example 3 | | 700 | 40 μm | 340° C. | Not carried out | 95% or more |
| Example 4 | | 300 | 40 μm | 340° C. | Not carried out | 95% or more |
| Comparative Example 1 | Polyamide | — | 75 μm | — | — | 95% or less |

From Table 1, it was found that each of the Examples is generally superior to the Comparative Example in the metal removal rate, and in particular, it is far superior to Comparative Example 1 in which the nylon porous membrane was used. Since each of the Examples has a high removal rate with a smaller film thickness than the Comparative Example, when a polyimide-based resin porous membrane is used for a filter medium or a filter device, it is possible to reduce the thickness of the medium or the size of the device. Even when processing the porous polyimide-based resin membrane into a fold shape, it can be folded many times, so it is possible to prepare a filter device having higher removal capability. It was found from Examples 1 and 2 and Examples 3 and 4 that chemical etching as an imide bond ring-opening step improved the metal removal rate.

In Comparative Example 1 in which porous membrane made of nylon was used, it was found that the metal removal rate was far lower.

The invention claimed is:

1. A purification method for purifying a silicon compound-containing liquid as an object to be purified, the method comprising:
   allowing some or all of the silicon compound-containing liquid to permeate through a polyimide and/or polyamideimide porous membrane having communicating pores from one side to the other side by way of a differential pressure,
   wherein the silicon compound-containing liquid comprises a silicon compound capable of producing a silanol group by hydrolysis.

2. The purification method according to claim 1, wherein the silicon compound-containing liquid is a silylating agent liquid, a film forming material, or a diffusing agent composition that is used for diffusing a dopant into a semiconductor substrate.

3. The purification method according to claim 1, wherein the object to be purified is a silylating agent liquid, the silicon compound is a silylating agent represented by the following general formula (1):

$$(R^{a1})_a Si(H)_b X^1_{4-a-b} \quad (1)$$

wherein in the formula (1), $R^{a1}$ each independently represents a monovalent organic group comprising a monovalent hydrocarbon group having 1 to 18 carbon atoms in which some or all of hydrogen atoms may be substituted with a fluorine atom; $X^1$ each independently represents a monovalent functional group in which an atom bonded to a silicon atom is nitrogen; a is an integer of 1 to 3; b is an integer of 0 to 2; and a total of a and b is 1 to 3.

4. The purification method according to claim 1, wherein the object to be purified is a film forming material, and the silicon compound is represented by the following general formula (2):

$$R^{a2}_{4-n2} SiX_{n2} \quad (2)$$

wherein in the formula (2), $R^{a2}$ is a hydrogen atom or a monovalent hydrocarbon group;
X is a group selected from the group consisting of a linear or branched alkoxy group having 1 to 5 carbon atoms, an isocyanate group, and a halogen atom; and
n2 is an integer of 1 to 4.

5. The purification method according to claim 1, wherein the silicon compound is represented by the following general formula (3):

$$R^{a3}_{4-n3}-Si(NCO)_{n3} \quad (3)$$

wherein in the formula (3), $R^{a3}$ is a hydrogen atom or a monovalent hydrocarbon group, and n3 is 2 to 4.

6. The purification method according to claim 5, wherein the object to be purified is used for forming a flattened film, an insulating film, a high refractive film, a resin layer for imprinting, or an etching mask.

7. The purification method according to claim 1, wherein the object to be purified is a diffusing agent composition further comprising a dopant and to be used for diffusing the dopant into a semiconductor substrate.

8. The purification method according to claim 7, wherein the silicon compound is a compound represented by the following general formula (4):

$$R^{a4}_{4-n4} Si(NCO)_{n4} \quad (4)$$

wherein in the formula (4), $R^{a4}$ is a hydrocarbon group, and n4 is an integer of 3 or 4.

9. The purification method according to claim 1, wherein some or all of impurities, comprising elements being solid at ordinary temperature temperature, contained in the object to be purified is removed from the object to be purified by the porous membrane.

10. The purification method according to claim 1, wherein the differential pressure is applied by using at least one selected from the group consisting of a hydraulic pressure, a vacuum, and a positive pressure of inert gas or nonreactive gas.

11. The purification method according to claim 1, wherein the communicating pores have a structure comprising substantially spherical pores that have an average spherical diameter of 50 to 5000 nm and are mutually connected to one another.

12. The purification method according to claim 11, wherein the substantially spherical pores further comprise a recess in an inner surface.

13. The purification method according to claim 1, wherein the communicating pores comprise a communicating pore having a pore diameter of 1 to 200 nm.

14. A method for producing a silylating agent liquid, a film forming material or a diffusing agent composition, wherein the method uses the purification method as defined in claim 1.

15. A method of forming a flattened film, an insulating film, a high refractive film, a resin layer for imprinting, or an etching mask, which comprises: using the object purified by the purification method according to claim 1.

16. A method of forming a flattened film, an insulating film, a high refractive film, a resin layer for imprinting, or an etching mask, the method comprising: purifying a silicon compound-containing liquid by the purification method according to claim 1.

17. A purification method for purifying a silicon compound-containing liquid as an object to be purified, the method comprising:
allowing some or all of the silicon compound-containing liquid to permeate through a filter medium comprising a polyimide and/or polyamideimide porous membrane having communicating pores from one side to the other side by way of a differential pressure,
wherein the silicon compound-containing liquid comprises a silicon compound capable of producing a silanol group by hydrolysis.

18. A purification method for purifying a silicon compound-containing liquid as an object to be purified, the method comprising:
allowing some or all of the silicon compound-containing liquid to permeate through a filter device comprising a polyimide and/or polyamideimide porous membrane having communicating pores from one side to the other side by way of a differential pressure,
wherein the silicon compound-containing liquid comprises a silicon compound capable of producing a silanol group by hydrolysis.

* * * * *